(12) United States Patent
Bonutti et al.

(10) Patent No.: US 8,012,108 B2
(45) Date of Patent: Sep. 6, 2011

(54) RANGE OF MOTION SYSTEM AND METHOD

(75) Inventors: Peter M. Bonutti, Effingham, IL (US);
Glen A. Phillips, Effingham, IL (US);
Justin E. Beyers, Effingham, IL (US)

(73) Assignee: Bonutti Research, Inc., Effingham, IL (US)

( * ) Notice: Subject to any disclaimer, the term of this patent is extended or adjusted under 35 U.S.C. 154(b) by 218 days.

(21) Appl. No.: 11/203,516

(22) Filed: Aug. 12, 2005

(65) Prior Publication Data
US 2007/0038161 A1    Feb. 15, 2007

(51) Int. Cl.
*A61H 1/02*    (2006.01)
(52) U.S. Cl. .............................. 601/5; 601/33
(58) Field of Classification Search .............. 601/5, 23, 601/24, 26, 27–35, 40, 97, 98, 101, 104
See application file for complete search history.

(56) References Cited

U.S. PATENT DOCUMENTS

| | | |
|---|---|---|
| 433,227 A | 7/1890 | Beacock |
| 2,191,283 A | 2/1940 | Longfellow |
| 2,206,902 A | 7/1940 | Kost |
| 2,223,276 A | 11/1940 | Ward |
| 2,237,252 A | 4/1941 | Longfellow |
| 2,246,689 A | 6/1941 | Kost |
| 2,250,493 A | 7/1941 | Milne |
| 2,590,729 A | 3/1952 | Scognamillo |
| 2,590,739 A | 3/1952 | Wanner et al. |
| 2,811,154 A | 10/1957 | Scholl |
| 2,820,455 A | 1/1958 | Hall |
| 2,829,562 A | 4/1958 | La Rue |
| 2,832,334 A | 4/1958 | Whitelaw |
| 3,083,708 A | 4/1963 | Gottfried |
| 3,338,237 A | 8/1967 | Sconce |
| 3,351,055 A | 11/1967 | Gottfried |
| 3,548,818 A | 12/1970 | Kaplan |
| 3,580,248 A | 5/1971 | Larson |
| 3,698,389 A | 10/1972 | Guedel |
| 3,701,349 A | 10/1972 | Larson |
| 3,724,452 A | 4/1973 | Nitschke |
| 3,760,056 A | 9/1973 | Rudy |
| 3,795,243 A | 3/1974 | Miller |
| 3,811,434 A | 5/1974 | Jacobson et al. |
| 3,814,419 A | 6/1974 | Bjorklund et al. |

(Continued)

FOREIGN PATENT DOCUMENTS

CA    2066151    10/1992
(Continued)

OTHER PUBLICATIONS

Advertising materials from the Internet on Jun. 5, 1998 entitled: "Quadrant by Smith & Nephew DonJoy". "Entering a New Plane".

(Continued)

*Primary Examiner* — Danton DeMille
(74) *Attorney, Agent, or Firm* — Armstrong Teasdale LLP

(57) ABSTRACT

The application is directed to devices and methods useful for expanding the range of motion of joints based on principles of stress relaxation and creep. Expanded range of motion is achieved by placing body parts near the joint in positions that stretch tissue around the joint. Even when the device is in any one position, it can impart forces on the body members to urge them to stretch surrounding tissue even further.

35 Claims, 19 Drawing Sheets

U.S. PATENT DOCUMENTS

| | | |
|---|---|---|
| 3,856,004 A | 12/1974 | Cox |
| 3,955,565 A | 5/1976 | Johnson, Jr. |
| 3,970,316 A | 7/1976 | Westmoreland, Jr. |
| 3,976,057 A | 8/1976 | Barclay |
| 4,039,183 A | 8/1977 | Sakurada |
| 4,076,022 A | 2/1978 | Walker |
| 4,084,267 A | 4/1978 | Zadina |
| 4,108,170 A | 8/1978 | Spann |
| 4,180,870 A | 1/1980 | Radulovic et al. |
| 4,214,577 A | 7/1980 | Hoy |
| 4,229,001 A | 10/1980 | Roman |
| 4,237,873 A | 12/1980 | Terry et al. |
| 4,241,731 A | 12/1980 | Pauley |
| 4,273,113 A | 6/1981 | Hofstein |
| 4,285,773 A | 8/1981 | Taciuk |
| 4,320,748 A | 3/1982 | Racette et al. |
| 4,363,481 A | 12/1982 | Erickson |
| 4,370,977 A | 2/1983 | Mauldin et al. |
| 4,383,523 A | 5/1983 | Schurman |
| 4,417,569 A | 11/1983 | Brudny |
| 4,441,489 A | 4/1984 | Evans et al. |
| 4,454,871 A | 6/1984 | Mann et al. |
| 4,456,001 A | 6/1984 | Pescatore |
| 4,456,002 A | 6/1984 | Barber et al. |
| 4,502,470 A | 3/1985 | Kiser et al. |
| 4,502,681 A | 3/1985 | Blomqvist |
| 4,508,111 A | 4/1985 | Hepburn |
| 4,509,509 A | 4/1985 | Bouvet et al. |
| 4,538,595 A | 9/1985 | Hajianpour |
| 4,538,600 A | 9/1985 | Hepburn |
| 4,570,619 A | 2/1986 | Gamm |
| 4,576,151 A | 3/1986 | Carmichael et al. |
| 4,589,406 A | 5/1986 | Florek |
| 4,606,542 A | 8/1986 | Segal |
| 4,612,919 A | 9/1986 | Best |
| 4,628,913 A | 12/1986 | Lerman |
| 4,641,639 A | 2/1987 | Padilla |
| 4,653,479 A | 3/1987 | Maurer |
| 4,665,905 A | 5/1987 | Brown |
| 4,693,239 A | 9/1987 | Clover, Jr. |
| 4,716,889 A | 1/1988 | Saringer |
| 4,718,665 A | 1/1988 | Airy et al. |
| 4,727,865 A | 3/1988 | Hill-Byrne |
| 4,739,334 A | 4/1988 | Soref |
| 4,765,320 A | 8/1988 | Lindemann et al. |
| 4,788,941 A | 12/1988 | Villeneuve |
| 4,790,301 A | 12/1988 | Silfverskiold |
| 4,793,334 A | 12/1988 | McGuinness et al. |
| 4,805,601 A | 2/1989 | Eischen, Sr. |
| 4,807,601 A | 2/1989 | Wright |
| 4,809,688 A | 3/1989 | Aymerica del Valle et al. |
| 4,834,073 A * | 5/1989 | Bledsoe et al. .................. 601/34 |
| 4,844,094 A | 7/1989 | Grim |
| 4,844,454 A | 7/1989 | Rogers |
| 4,844,455 A | 7/1989 | Funkhouser, Jr. |
| 4,848,326 A | 7/1989 | Lonardo |
| 4,862,877 A | 9/1989 | Barber |
| 4,865,024 A | 9/1989 | Hensley et al. |
| 4,869,267 A | 9/1989 | Grim et al. |
| 4,869,499 A | 9/1989 | Schiraldo |
| 4,884,454 A | 12/1989 | Johnson |
| 4,913,135 A | 4/1990 | Mattingly |
| 4,913,755 A | 4/1990 | Grim |
| 4,930,497 A | 6/1990 | Saringer |
| 4,953,543 A | 9/1990 | Grim et al. |
| 4,955,369 A | 9/1990 | Bledsoe et al. |
| 4,955,396 A | 9/1990 | Fralick et al. |
| 4,957,281 A | 9/1990 | Christolear, Jr. |
| 4,964,402 A | 10/1990 | Grim et al. |
| 4,991,234 A | 2/1991 | Greenberg |
| 4,996,979 A | 3/1991 | Grim et al. |
| 5,005,563 A | 4/1991 | Veale |
| 5,018,514 A | 5/1991 | Grood et al. |
| 5,019,050 A | 5/1991 | Lynn et al. |
| 5,025,782 A | 6/1991 | Salerno |
| 5,027,688 A | 7/1991 | Suzuki et al. |
| 5,027,801 A | 7/1991 | Grim |
| 5,027,802 A | 7/1991 | Donohue |
| 5,036,837 A | 8/1991 | Mitchell et al. |
| 5,036,838 A | 8/1991 | Sherman |
| 5,052,375 A * | 10/1991 | Stark et al. .................. 601/34 |
| 5,070,866 A | 12/1991 | Alexander et al. |
| 5,078,128 A | 1/1992 | Grim et al. |
| 5,088,481 A | 2/1992 | Darby |
| 5,100,403 A | 3/1992 | Hotchkiss et al. |
| 5,102,411 A | 4/1992 | Hotchkiss et al. |
| 5,116,359 A | 5/1992 | Moore |
| 5,125,400 A | 6/1992 | Johnson, Jr. |
| 5,135,470 A | 8/1992 | Reeves |
| 5,139,475 A | 8/1992 | Robicsek |
| 5,141,489 A | 8/1992 | Sereboff |
| 5,156,589 A | 10/1992 | Langen et al. |
| 5,163,451 A | 11/1992 | Grellas |
| 5,167,612 A | 12/1992 | Bonutti |
| 5,191,903 A | 3/1993 | Donohue |
| 5,197,942 A | 3/1993 | Brady |
| 5,201,702 A | 4/1993 | Mars |
| 5,201,772 A | 4/1993 | Maxwell |
| 5,203,321 A | 4/1993 | Donovan et al. |
| 5,211,161 A | 5/1993 | Stef |
| 5,213,094 A | 5/1993 | Bonutti |
| 5,213,095 A | 5/1993 | Dague |
| 5,218,954 A | 6/1993 | van Bemmelen |
| 5,226,245 A | 7/1993 | Lamont |
| 5,232,435 A | 8/1993 | Leibinsohn |
| 5,252,101 A | 10/1993 | Rosenwinkel et al. |
| 5,252,102 A | 10/1993 | Singer et al. |
| 5,261,125 A | 11/1993 | Cartwright et al. |
| 5,277,695 A | 1/1994 | Johnson, Jr. et al. |
| 5,285,773 A | 2/1994 | Bonutti et al. |
| 5,297,540 A | 3/1994 | Kaiser et al. |
| 5,312,322 A | 5/1994 | Santana |
| 5,316,022 A | 5/1994 | Schiek, Sr. |
| 5,323,435 A | 6/1994 | Baversten |
| RE34,661 E | 7/1994 | Grim |
| 5,327,882 A | 7/1994 | Saringer et al. |
| 5,328,448 A | 7/1994 | Gray, Sr. |
| 5,329,705 A | 7/1994 | Grim et al. |
| 5,348,530 A | 9/1994 | Grim et al. |
| 5,349,956 A | 9/1994 | Bonutti |
| 5,352,216 A | 10/1994 | Shiono et al. |
| 5,354,260 A | 10/1994 | Cook |
| 5,364,323 A | 11/1994 | Liu |
| 5,365,947 A | 11/1994 | Bonutti |
| 5,370,133 A | 12/1994 | Darby et al. |
| 5,372,597 A | 12/1994 | Hotchkiss et al. |
| 5,376,091 A | 12/1994 | Hotchkiss et al. |
| 5,378,223 A | 1/1995 | Grim et al. |
| 5,385,536 A | 1/1995 | Burkhead et al. |
| 5,389,065 A | 2/1995 | Johnson, Jr. |
| 5,391,132 A | 2/1995 | Greenwald |
| 5,395,303 A | 3/1995 | Bonutti et al. |
| 5,399,152 A | 3/1995 | Habermeyer et al. |
| 5,403,265 A | 4/1995 | Berguer et al. |
| 5,407,420 A | 4/1995 | Bastyr et al. |
| 5,407,422 A | 4/1995 | Matthijs et al. |
| 5,417,643 A | 5/1995 | Taylor |
| 5,419,757 A | 5/1995 | Daneshvar |
| 5,421,874 A | 6/1995 | Pearce |
| 5,435,009 A | 7/1995 | Schild et al. |
| 5,437,611 A | 8/1995 | Stern |
| 5,452,205 A | 9/1995 | Telepko |
| 5,453,075 A | 9/1995 | Bonutti et al. |
| 5,453,082 A * | 9/1995 | Lamont .................. 602/27 |
| 5,456,268 A * | 10/1995 | Bonutti .................. 128/898 |
| 5,456,286 A | 10/1995 | Warner et al. |
| 5,464,385 A | 11/1995 | Grim |
| 5,466,213 A | 11/1995 | Hogan et al. |
| 5,466,250 A | 11/1995 | Johnson, Jr. et al. |
| 5,472,407 A | 12/1995 | Schenck |
| 5,492,133 A | 2/1996 | McVicker |
| 5,503,619 A | 4/1996 | Bonutti |
| 5,503,622 A | 4/1996 | Wehr |
| 5,503,908 A | 4/1996 | Faass |
| 5,518,009 A | 5/1996 | Ruiz-Gonzalez |
| 5,520,181 A | 5/1996 | Kreidler et al. |
| 5,520,628 A | 5/1996 | Wehr |

| Patent No. | Date | Name |
|---|---|---|
| 5,527,269 A | 6/1996 | Reithofer |
| 5,531,669 A | 7/1996 | Varnau |
| 5,535,274 A | 7/1996 | Braitberg et al. |
| 5,538,486 A | 7/1996 | France et al. |
| 5,571,077 A | 11/1996 | Klearman et al. |
| 5,577,998 A | 11/1996 | Johnson, Jr. et al. |
| 5,605,535 A | 2/1997 | Lepage |
| 5,609,570 A | 3/1997 | Lamont |
| 5,611,764 A | 3/1997 | Bonutti et al. |
| 5,620,411 A | 4/1997 | Schumann et al. |
| 5,626,537 A | 5/1997 | Danyo et al. |
| 5,647,378 A | 7/1997 | Farnum |
| 5,653,680 A | 8/1997 | Cruz |
| 5,665,059 A | 9/1997 | Klearman et al. |
| 5,681,269 A | 10/1997 | Basaj et al. |
| 5,685,830 A | 11/1997 | Bonutti |
| 5,755,679 A | 5/1998 | Selner et al. |
| 5,761,834 A | 6/1998 | Grim et al. |
| 5,772,619 A | 6/1998 | Corbett |
| 5,778,565 A | 7/1998 | Holt et al. |
| 5,788,659 A | 8/1998 | Haas |
| 5,792,084 A | 8/1998 | Wilson et al. |
| 5,820,577 A | 10/1998 | Taylor |
| 5,823,975 A | 10/1998 | Stark et al. |
| 5,833,639 A | 11/1998 | Nunes et al. |
| 5,839,139 A | 11/1998 | Fink |
| 5,848,979 A | 12/1998 | Bonutti et al. |
| 5,865,773 A | 2/1999 | Koledin |
| 5,882,320 A | 3/1999 | Peterson |
| 5,882,323 A | 3/1999 | Belkin |
| 5,919,148 A | 7/1999 | Marko et al. |
| 5,929,782 A | 7/1999 | Stark et al. |
| 5,940,992 A | 8/1999 | Darby |
| 5,943,705 A | 8/1999 | Sink |
| 5,980,435 A | 11/1999 | Joutras et al. |
| 6,007,500 A | 12/1999 | Quintinskie, Jr. |
| 6,021,780 A | 2/2000 | Darby |
| 6,027,468 A | 2/2000 | Pick |
| 6,053,169 A | 4/2000 | Hunt |
| 6,059,576 A | 5/2000 | Brann |
| 6,093,162 A | 7/2000 | Fairleigh et al. |
| 6,099,489 A | 8/2000 | Herzberg et al. |
| 6,113,562 A | 9/2000 | Bonutti et al. |
| 6,142,964 A | 11/2000 | Gilmour |
| 6,142,965 A | 11/2000 | Mathewson |
| 6,155,994 A * | 12/2000 | Hubbard et al. ................. 601/5 |
| 6,179,747 B1 | 1/2001 | Kelley |
| 6,179,800 B1 | 1/2001 | Torrens |
| 6,184,797 B1 | 2/2001 | Stark et al. |
| 6,228,044 B1 | 5/2001 | Jensen et al. |
| 6,267,742 B1 | 7/2001 | Krivosha et al. |
| 6,296,595 B1 | 10/2001 | Stark et al. |
| 6,371,123 B1 | 4/2002 | Stark et al. |
| 6,384,755 B1 | 5/2002 | Hayden |
| 6,409,691 B1 | 6/2002 | Dakin et al. |
| 6,436,058 B1 | 8/2002 | Krahner et al. |
| 6,485,447 B1 | 11/2002 | Lavery et al. |
| 6,502,577 B1 | 1/2003 | Bonutti |
| 6,503,213 B2 | 1/2003 | Bonutti |
| 6,509,659 B1 | 1/2003 | Carroll et al. |
| 6,572,571 B2 | 6/2003 | Lowe |
| 6,575,926 B2 | 6/2003 | Bonutti |
| 6,599,255 B2 | 7/2003 | Zhang |
| 6,599,263 B1 | 7/2003 | Bonutti et al. |
| 6,637,429 B2 | 10/2003 | Mundrick et al. |
| 6,682,497 B2 | 1/2004 | Jensen et al. |
| 6,702,768 B2 * | 3/2004 | Mano et al. ................. 601/29 |
| 6,743,187 B2 | 6/2004 | Solomon et al. |
| 6,770,047 B2 | 8/2004 | Bonutti |
| 6,872,187 B1 * | 3/2005 | Stark et al. ................. 602/16 |
| 6,890,285 B2 | 5/2005 | Rahman et al. |
| 6,921,377 B2 | 7/2005 | Bonutti |
| 6,929,616 B2 | 8/2005 | Bonutti et al. |
| 6,958,048 B2 | 10/2005 | Bonutti |
| 6,974,431 B2 | 12/2005 | Jensen |
| 6,984,197 B2 * | 1/2006 | Sugiyama et al. ............. 482/148 |
| 7,112,179 B2 | 9/2006 | Bonutti et al. |
| 7,182,738 B2 | 2/2007 | Bonutti et al. |
| 7,204,814 B2 | 4/2007 | Peles |
| 7,306,573 B2 | 12/2007 | Bonutti |
| 7,404,804 B2 | 7/2008 | Bonutti |
| 2001/0047209 A1 | 11/2001 | Solomon |
| 2002/0029784 A1 | 3/2002 | Stark |
| 2002/0183655 A1 | 12/2002 | Zhang |
| 2004/0153010 A1 | 8/2004 | Bonutti |
| 2004/0215120 A1 | 10/2004 | Jensen |
| 2004/0243025 A1 * | 12/2004 | Peles ................. 601/5 |
| 2006/0036205 A1 | 2/2006 | Bonutti |
| 2007/0038161 A1 | 2/2007 | Bonutti et al. |
| 2007/0055190 A1 | 3/2007 | Bonutti et al. |
| 2007/0100267 A1 | 5/2007 | Bonutti et al. |
| 2007/0135738 A1 | 6/2007 | Bonutti et al. |
| 2007/0197605 A1 | 8/2007 | Glombik et al. |
| 2007/0219475 A1 | 9/2007 | Bonutti et al. |
| 2007/0219476 A1 | 9/2007 | Bonutti et al. |
| 2008/0091132 A1 | 4/2008 | Bonutti |
| 2008/0188356 A1 | 8/2008 | Bonutti |

FOREIGN PATENT DOCUMENTS

| | | |
|---|---|---|
| CA | 2065669 | 10/1993 |
| DE | 405327 | 10/1924 |
| DE | 2829562 | 1/1980 |
| DE | G 8806231.7 | 5/1988 |
| EP | 0181668 | 5/1986 |
| EP | 0181688 | 5/1986 |
| EP | 0380060 | 1/1990 |
| EP | 0510840 | 10/1992 |
| FR | 2661333 | 4/1990 |
| JP | 4261657 | 9/1992 |
| JP | 2001 087296 | 4/2001 |
| SU | 1158195 | 5/1985 |
| SU | 1426580 | 9/1988 |
| SU | 1671296 | 8/1991 |
| WO | WO 88/04543 | 6/1988 |
| WO | WO 2004/007314 | 1/2004 |
| WO | WO 2005/086741 | 9/2005 |
| WO | WO 2007/051168 | 5/2007 |
| WO | WO 2007/109638 | 9/2007 |
| WO | WO 2008/036895 | 8/2008 |

OTHER PUBLICATIONS

Advertising materials from the Internet on Jun. 5, 1998 entitled: "Make DonJoy's Quadrant Your First Choice for Effective Post-Operative Shoulder Treatment". "Quadrant Brace Specifications".
Advertising materials from the Internet on Jun. 5, 1998 entitled: "Ultraslingtm by DonJoy".
Neporent et al. "Weight Training for Dummies" 1997, p. 294.
Dynasplint Systems Inc., "Practitioner Information for Dynasplint LPS Orthosis- Knee Extension", date known but prior to Aug. 23, 1991.
Publication by UE Tech, Technology Meeting Human Needs, Rehabilitation Product Catalog, vol. 7, publication date unknown, but prior to Oct. 13, 1998.
Taber's Cyclopedic Medical Dictionary 16th Edition (1989) (#34), p. 521, definition of "distraction".

* cited by examiner

RANGE OF MOTION SYSTEM AND METHOD

FIELD OF THE INVENTION

The present invention relates to an adjustable orthosis for stretching tissue in the human body. In particular, the present invention relates to an adjustable orthosis which utilizes the principles of stress relaxation and creep for stretching tissue such as ligaments, tendons or muscles around a joint during flexion or extension of the joint.

BACKGROUND OF THE INVENTION

In a joint, the range of motion depends upon the anatomy and condition of that joint and on the particular genetics of each individual. Many joints primarily move either in flexion or extension, although some joints also are capable of rotational movement in varying degrees. Flexion is to bend the joint and extension is to straighten the joint; however, in the orthopedic convention some joints only flex. Some joints, such as the knee, may exhibit a slight internal or external rotation during flexion or extension. Other joints, such as the elbow or shoulder, not only flex and extend but also exhibit more rotational range of motion, which allows them to move in multiple planes. The elbow joint, for instance, is capable of supination and pronation, which is rotation of the hand about the longitudinal axis of the forearm placing the palm up or the palm down. Likewise, the shoulder is capable of a combination of movements, such as abduction, internal rotation, external rotation, flexion and extension.

Most people do not appreciate the complexity of joint motion until something goes wrong, such as when an injury results in lost range of motion. When a joint is injured, either by trauma or by surgery, scar tissue can form or tissue can contract and consequently limit the range of motion of the joint. For example, adhesions can form between tissues and the muscle can contract itself with permanent muscle contracture or tissue hypertrophy such as capsular tissue or skin tissue. Lost range of motion may also result from trauma such as excessive temperature (e.g., thermal or chemical burns) or surgical trauma so that tissue planes which normally glide across each other may become adhered together to markedly restrict motion. The adhered tissues may result from chemical bonds, tissue hypertrophy, proteins such as Actin or Myosin in the tissue, or simply from bleeding and immobilization. It is often possible to mediate, and possibly even correct this condition by use of a range-of-motion (ROM) orthosis, but the longer the period of stiffness or loss of motion the greater the time interval and the force required to regain lost range of motion. Therefore, it is beneficial to treat the tissue or joint as early as possible. For example, a ROM orthosis may be applied immediately after surgery or as soon as the stiffness problem is diagnosed.

ROM orthoses are used during physical rehabilitative therapy to increase the range-of-motion of a joint. Additionally, they also may be used for tissue transport, bone lengthening, stretching of skin or other tissue, tissue fascia, and the like. When used to treat a joint, the device typically is attached on opposite members of the joint so that is can apply a force to move the joint in opposition to the contraction.

A number of different configurations and protocols may be used to increase the range of motion of a joint. For example, stress relaxation techniques may be used to apply variable forces to the joint or tissue while in a constant position. "Stress relaxation" is the reduction of forces, over time, in a material that is stretched and held at a constant length. Relaxation occurs because of the realignment of fibers and elongation of the material when the tissue is held at a fixed position over time. Treatment methods that use stress relaxation are serial casting and static splinting. One example of devices utilizing stress relaxation is the Joint Active System, which uses a rack and pinion gear to move and hold the joint in a constant position.

Sequential application of stress relaxation techniques, also known as Static Progressive Stretch ("SPS") uses the biomechanical principles of stress relaxation to restore range of motion (ROM) in joint contractures. SPS is the incremental application of stress relaxation—stretch to position to allow tissue forces to drop as tissues stretch, and then stretching the tissue further by moving the device to a new position—repeated application of constant displacement with variable force. In an SPS protocol, the patient is fitted with an orthosis about the joint. The orthosis is operated to stretch the joint until there is tissue/muscle resistance. The orthosis maintains the joint in this position for a set time period, for example five minutes, allowing for stress relaxation. The orthosis is then operated to incrementally increase the stretch in the tissue and again held in position for the set time period. The process of incrementally increasing the stretch in the tissue is continued, with the pattern being repeated for a maximum total session time, for example 30 minutes. The protocol can be progressed by increasing the time period, total treatment time, or with the addition of sessions per day. Additionally, the applied force may also be increased.

Exemplary orthoses that utilize the stress relaxation and/or SPS protocols include, but are not limited to, those described in U.S. Pat. No. 6,921,377 ("Finger Orthosis"), U.S. Pat. No. 6,770,047 ("Method of using a neck brace"), U.S. Pat. No. 6,599,263 ("Shoulder Orthosis"), U.S. Pat. No. 6,113,562 ("Shoulder Orthosis"), U.S. Pat. No. 6,503,213 ("Method of using a neck brace"), U.S. Pat. No. 6,502,577 ("Finger Orthosis"), U.S. Pat. No. 5,848,979 ("Orthosis"), U.S. Pat. No. 5,685,830 ("Adjustable Orthosis Having One-Piece Connector Section for Flexing"), U.S. Pat. No. 5,611,764 ("Method of Increasing Range of Motion"), U.S. Pat. No. 5,503,619 ("Orthosis for Bending Wrists"), U.S. Pat. No. 5,456,268 ("Adjustable Orthosis"), U.S. Pat. No. 5,453,075 ("Orthosis with Distraction through Range of Motion"), U.S. Pat. No. 5,395,303 ("Orthosis with Distraction through Range of Motion"), U.S. Pat. No. 5,365,947 ("Adjustable Orthosis"), U.S. Pat. No. 5,285,773 ("Orthosis with Distraction through Range of Motion"), U.S. Pat. No. 5,213,095 ("Orthosis with Joint Distraction"), and U.S. Pat. No. 5,167,612 ("Adjustable Orthosis"), and U.S. Publication No. 20040215111 ("Patient monitoring apparatus and method for orthosis and other devices"), all to Bonutti and herein are expressly incorporated by reference in their entirety. It should be noted that the SPS protocol is disclosed in a number of the above-identified patents. It should be further noted that the mark STATIC PROGRESSIVE STRETCH COMPANY is a registered trademark of Joint Active Systems, Inc (Effingham, Ill.).

Another treatment protocol uses principles of creep to apply a constant force over variable displacement. In other words, techniques and devices utilizing principles of creep involve continued deformation with the application of a fixed load. For tissue, the deformation and elongation are continuous but slow (requiring hours to days to obtain plastic deformation), and the material is kept under a constant state of stress. Treatment methods such as traction therapy and dynamic splinting are based on the properties of creep.

One potential disadvantage of using a static load, however, is that the amount of force needed to effect tissue stretching or creep may change over time. For instance, while a 10 lb force may initially provide desirable results in the beginning of the treatment protocol, it may be insufficient after the tissue has begun to stretch. Likewise, the amount of force needed in the beginning of the treatment protocol may be too much force for use in later stages of the protocol.

Exemplary orthoses utilizing the creep protocol include U.S. Pat. Nos.; 5,167,612, 5,365,947, and 5,456,268 entitled "Adjustable Orthosis", and U.S. Pat. No. 5,685,830 entitled "Adjustable Orthosis having one-piece connector section for flexing" all to Bonutti; U.S. Pat. No. 6,413,231, entitled "Device To Assist In Therapy Of Patient Who Has Limited Jaw Opening;" U.S. Pat. No. 5,645,521, entitled "Shoulder Physical Therapy Device;" U.S. Pat. No. 5,070,868, entitled "Adjustable Splint;" and U.S. Pat. No. 4,947,835, entitled "Adjustable splint assembly;" all to assigned to Dynasplint System Inc. and all of which herein are expressly incorporated by reference in their entirety. Another example of orthoses utilizing the creep protocol include U.S. Pat. No. 5,472, 410 to Hammersly, entitled "Adjustable Flexion and Extension Joint Orthoses," and U.S. Pat. No. 5,437,619 to Malewicz et al., entitled "Range-of-Motion Splint with Eccentric Spring," both of which are expressly incorporated by reference in their entirety.

In the past, treatment protocols and related devices utilized either stress relaxation or creep, but not both.

SUMMARY OF THE INVENTION

The present invention is directed to devices and methods of using a combination of stress relaxation and creep protocols to treat contractures. Without being bound to a particular theory, it is believed that combining these loading conditions, such as by applying them in a Static Progressive Stretch mode, may reduce the overall treatment time or may improve the overall amount of tissue stretch achieved.

One embodiment of the invention relates to a device for stretching tissue around a joint between two pivotable or rotatable body portions near a joint. The device has two arm members that are connected to the body portions near the joint. A drive assembly is used to move one arm member relative to the other so that the arm can be moved, for instance, from a first position to a second position. The drive assembly also may be capable of moving the arm to a third, fourth, or even more positions or configurations.

A force application assembly associated with one of the arm members then imparts forces to one of the body portions. The force application assembly may be interposed between an arm member and body portion, and may include one or more springs, such as a linear spring, leaf spring, helical spring, torsional spring, or the like, that help impart forces on the patient's body. Alternatively, the force application assembly may use a fluid bladder or have resilient material that imparts forces on the body.

The force application also could be dynamic tension. The dynamic tension could be a known spring which can have adjustable control, vary the force, could have a control knob or could be electrically controlled or could be controlled via sensor. Springs and other components used in the present invention may be formed of low-cost polymeric materials so that all or part of the device may be designed to be disposable. In addition, the force application assembly may have an adjustable controllable dynamic system that allows electrical feedback or compliance monitoring of the system. Some examples of feedback or monitoring systems that may be used with the invention are described in U.S. Publication No. 20040215111 entitled "Patient Monitoring Apparatus and Method for Orthosis and Other Devices" to Bonutti et al., the entirety of which is incorporated by reference.

The forces imparted to the body may be substantially constant, or alternatively may vary in degree, force profile, or duration. The device may hold the second arm in any of its positions for a predetermined period of time, until a desired amount of tissue stretch relaxation or creep is achieved, or until some other parameter is met. In some embodiments, one or more cuffs are used to attach one or more arm members to the patient's body. Depending on the desired treatment, a cuff and force application assembly may be configured to impart torsional forces on one of the body portions instead of, or in addition to, imparting bending forces. Axial forces may also be applied either alone or in combination with other types of forces.

The invention also is directed to methods of increasing the range of motion on connective tissue between first and second body portions interconnected by a joint. In particular, one embodiment of the invention involves connecting a first and second arm member with a first and second body portion, respectively. One of the arm members may then be moved from a first position to a second position, utilizing the principles of stress relaxation to stretch the tissue about the joint. While in this second position, a force may be imparted on a body member to urge it to move even further than the second position, utilizing the principles of creep to further stretch the tissue about the joint. This force may be applied throughout a treatment interval, or may vary in degree, force profile, or duration. Some embodiments involve moving the body member to third, fourth or even more positions. These multiple positions may gradually increase in a particular direction or range to account for stretching of the body tissue.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1A:
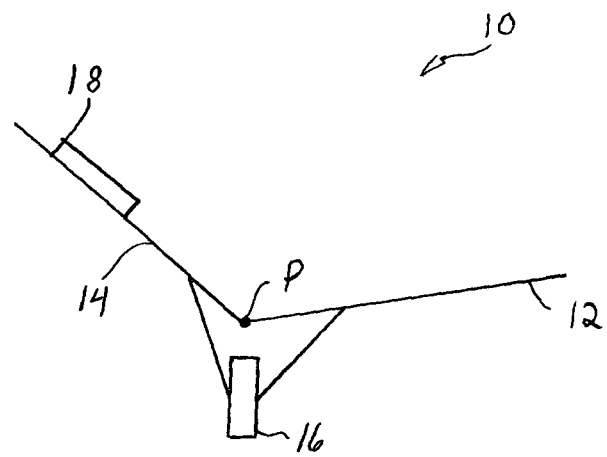
FIG. 1A is a schematic diagram of an orthosis including a drive assembly and a force application assembly.

The present invention relates to a ROM device for stretching tissue, such as the connective tissue around a joint, between first and second body portions utilizing the principles of stress relaxation and creep. As previously identified, treatment protocols based on principles of creep involve continued tissue movement and deformation under the application of constant loading, while treatment protocols based on principles of stress relaxation involve varying loading and constant displacement. Techniques utilizing principles of creep therefore allow joint position to change over time as tissue stretches in response to the applied load, whereas techniques utilizing stress relaxation maintain a constant joint position while allowing the applied load to vary over time—usually to diminish or lessen as the tissue stretches. Relaxation occurs because of the realignment of fibers and elongation of the material when the tissue is held at a fixed position over time. As explained in greater detail below, the invention also utilizes the principles of Static Progressive Stretch to provide a sequential application of stress relaxation and creep to the treated tissue. Using the following detailed description and examples, skilled artisans will recognize that it is possible to modify currently existing devices to include features of the present invention.

A joint and the first and second body portions can define on one side (the flexor side) of the joint an inner sector which decreases in angle as the joint is flexed (bent) and on the opposite side (the extensor side) of the joint an outer sector which decreases in angle as the joint is extended (straightened). The orthosis of the present invention is affixable to either the flexor or extensor side of the joint for treatment of flexion or extension contractures. In flexion and extension the joint may also exhibit slight internal or external rotations. As noted above, some joints may also be capable of even greater rotation. While the examples discussed herein primarily illustrate aspects of the invention in the context of increasing range of motion for flexion and extension, they also may be used to increase rotational range of motion.

The orthosis includes a drive assembly for moving the second body portion with respect to the first body portion from a first position to a second position. The orthosis fully or at least partially restricts motion of the second body portion in at least one direction (e.g. flexion, extension, or rotation), utilizing the principles of stress relaxation to stretch the tissue around the joint.

The orthosis further comprises a force application assembly that can apply loading to the tissue while the device is in one or more of its angular positions. The force applied by the force application assembly preferably is in a direction where joint or tissue movement is not fully restricted by the drive assembly or other components of the device. As explained below, the force application assembly can provide a constant force to the second body portion, may be capable of permitting adjustment of the force applied to the second body portion, or may be configured to provide a varying force profile across the second body portion. Initially, the force applied by the force application assembly may be less than the force applied by the drive assembly. As the force in the tissue drops, however, the drive assembly force may reduce to a point where the force application assembly provides a greater force on the tissue. The application of the force application assembly force results in a continuous stretching of the tissue around the joint, maintaining, decreasing, or preventing a relaxation of the tissue, utilizing the principles of creep to further stretch the joint tissue. When used together, the drive assembly and force application assembly take advantage of both principles of stress relaxation and creep.

After a set time period, the drive assembly may be used to move the second body portion from the second position to a third position, incrementally stretching the tissue surrounding the joint. Thus, the orthosis may be capable of moving from a first position to one or more other positions to provide different configuration angles of the device. It is contemplated that the drive assembly may be used to incrementally move the second body portion after the expiration of a predetermined time or until completion of the protocol. This approach is different from application of a constant load over a sustained time period.

Alternatively, the orthosis of the present invention can be used to effect rotational movement between bones in a body of a patient. For example, in a wrist joint it may be desirable to stretch viscoelastic body tissue connected with the ulna and radius bones and/or with the humerus in the arm of a patient in order to obtain a greater range of supination or pronation of the hand of the patient. During supination or pronation of a hand of a patient, the ulna and radius bones in the lower portion of the arm of the patient move relative to each other.

The drive assembly of the orthosis may be used to move the radius bones with respect to the ulna from a first position to a second position when in the second position. The orthosis may restrict movement of the radius bones in at least one direction, such as by preventing the radius and ulna from returning to the first position. In this manner, the drive assembly utilizes the principles of stress relaxation to stretch the tissue around the wrist joint. After a set time period, the drive assembly may be used to move the radius bones from the second position to a third position, incrementally stretching the tissue surrounding the wrist joint.

As previously explained, the force application assembly can apply loading to the radius bones while the drive assembly is in one or more positions. This allows the device to utilize the principles of creep to help stretch the tissue. Initially, the force applied by the force application assembly may be less than a force applied by the drive assembly. As the force in the tissue drops, the drive assembly force may reach a point where the force application assembly provides a greater force to the tissue. The forces applied by the force application assembly results in a continuous stretching of the tissue around the joint during the set time period, maintaining, decreasing, or preventing a relaxation of the tissue.

In addition, the forces applied by the drive assembly and force application assembly may be in substantially the same direction or alternatively may differ. For example, increasing range of motion for a knee may involve applying loading on the joint in substantially the same direction for both assemblies. In contrast, treatment of an ankle, wrist, elbow, or shoulder may involve the drive assembly applying a force to cause flexion or extension while the force application assembly applies rotational forces (or vice versa).

Referring now to the drawing figures in which like reference designators refer to like elements, there is shown in FIG. 1A schematic representation of the orthosis 10 of the present invention. The orthosis 10 includes a first arm member 12 attachable to a first body portion and a second arm member 14 attachable to a second body portion. In this embodiment, the first and second arms 12, 14 are pivotally connected to each other at the axis of rotation "P."

Figure 1B:
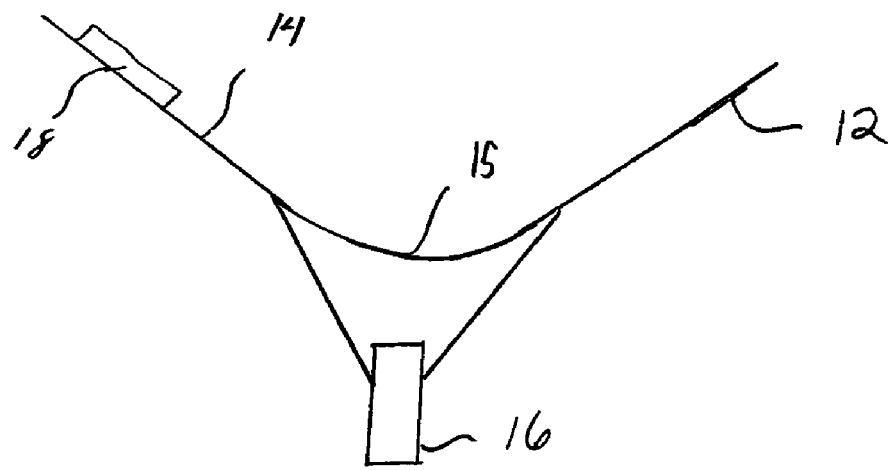
FIG. 1B is a schematic diagram of the orthosis of FIG. 1A including flexible connecting section.

Alternatively, as shown in FIG. 1B the first and second members 12 and 14 can be operatively connected with a living hinge or flexible section 15. In contrast to a point hinge connection, a flexible section 15 allows for a self centering connection, pivoting the first and second members 12 and 14 about a joint axis, as opposed to a hinge axis. For example, the first and second members 12 and 14 can be connected with a flexible section 15, such as a bar, which allows bending movement between the first and second members 12 and 14. The flexible section 15 can include stress risers, allowing for an easing on bending.

Figure 1C:
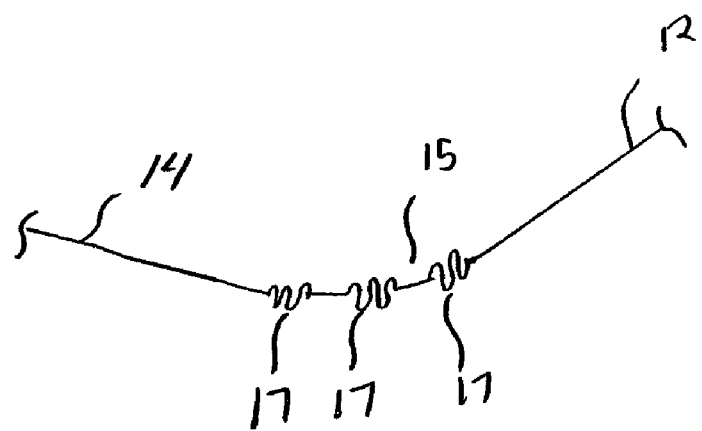
FIG. 1C is a schematic diagram of the flexible connecting section of FIG. 1B including an accordion section.

Additionally, as shown in FIG. 1C, the flexible section 15 can include an accordion section 17, allowing the flexible section 15 to expand and contract as it bends. For complex joints, such as a wrist joint, the flexible section 15 can include multiple accordion sections 17. The multiple accordion sections 17 allow the device to more closely emulate the joint dynamics.

The flexible section 15 can be made of a flexibly polymeric material, metal, or other biocompatible materials capable of exerting loading when flexed, stretched or compressed. An exemplary orthosis, including a flexible section is disclosed in U.S. Pat. No. 5,685,830 entitled "Adjustable Orthosis having one-piece connector section for flexing" to Bonutti, the contents of which are herein expressly incorporated by reference in their entirety.

Furthermore, the flexible section 15 can be made of a shape memory or reactive material. For example, the flexible section 15 can be made of a shape memory material, where a change in temperature results in a shape or position change of the flexible section 15. The change in shape of the flexible section 15 can be used to change the position of the first and second arm members 12 and 14. Alternatively, the change in shape of the flexible section 15 can be used to provide a force to the first and second arm members 12 and 14.

Similarly, the flexible section 15 can be made of a reactive material, where a change in temperature or an application of energy results in a change in the physical properties of the flexible section 15. For example, the flexible section 15 can initially be in a rigid form. An electric current can be applied to the flexible section 15, changing the flexible section 15 from rigid to flexible, allowing movement of the first and second arm members 12 and 14. Upon positioning the first and second arm members 12 and 14, the electric current can be discontinued, changing the flexible section 15 from flexible to rigid, securing the position of the first and second arm members 12 and 14.

A drive assembly 16 is connected to the first and second arm members 12 and 14, where the drive assembly 16 is operated to apply a force to rotate the first and second arm members 12 and 14 relative to each other about point "P." The drive assembly 16 may be connected to the first and second arm members 12 and 14 on the inner or outer sectors of the orthosis 10. Alternatively, the drive assembly 18 may be connected to a side portion of the orthosis 10, along the joint axis 16, or to other sectors of the orthosis 10.

The first arm member 12 can be secured to a first body portion of a patient and the second body member 14 can be secured to a second body portion of the patient, where a joint is interposed between the first and second arm members 12 and 14. The drive assembly 16 is actuated to provide a force to the second arm member 12 with respect to the first arm member 14, pivoting the second arm member 14 with respect to the first arm member 12 from a first position to a second position. The movement of the first and second arm members 12 and 14 rotates the first and second body portions with respect to each other about the joint axis. The orthosis 10 restricts movement of the second body portion in at least one direction when in the second position, utilizing the principles of stress relaxation to stretch the tissue around the joint.

The drive assembly 16 can further include a locking mechanism. The locking mechanism can be used to secure the position of the second arm member 14 with respect to the first arm member 12. The locking mechanism can prevent the actuation of the drive assembly 16, securing the position of first and second arm members 12 and 14. Alternatively, the locking mechanism can secure the first and second arm members 12 and 14, preventing an actuation of the drive assembly 16 from moving the first and second arm members 12 and 14. The locking mechanism can be utilized such that the orthosis 10 can be used as a static splint.

The orthosis 10 further includes a force application assembly 18 connected to the second member 14. The force application assembly 18 may be positioned between the second member 14 and the second body portion, such that the force application assembly 18 imparts loading forces to the second body portion with respect to the second arm member 14, utilizing the principles of creep to further stretch the joint tissue. The loading forces may be substantially constant or may vary in degree or duration.

Initially, the force applied by the force application assembly 18 may be less than a force applied by the drive assembly 16. As the tissue is stretched, however, it may relax and reduce the degree of resistance to the drive assembly position. In turn, the drive assembly force decreases and may reach a point where the force application assembly force exceeds the drive assembly force. The force application assembly 18 can impart a substantially constant force onto the second body portion, or alternatively may vary in degree or duration. The application of the force application assembly force utilizes the principles of creep to continuously stretch the joint tissue during the set time period, thereby maintaining, decreasing, or preventing a relaxation of the tissue.

After a set time period, the drive assembly 16 may be used to move the second arm member 14 with respect to the first arm member 12 from the second position to a third position, incrementally stretching the tissue surrounding the joint. It is contemplated that the drive assembly 12 may be used to incrementally move the second body portion after the expiration of a predetermined time or until completion of the protocol.

The orthosis 10 of the present invention can be connected to the flexor side of the first and second body portions of the joint, which results in a decrease in angle as the joint is flexed (bent) and an increase in angle as the joint is extended (straightened). Similarly, orthosis 10 of the present invention can be connected to the extensor side of the joint, which results in a decrease in angle as the joint is extended straightened and an increase in angle as the joint is flexed (bent).

In an exemplary use, the orthosis 10 is operated to extend a joint in the following manner. The first arm member 12 is fastened to the first body portion and the second arm member 14 is fastened to the second body portion. The orthosis 10 is attached to the first and second body portions in a first position. The drive assembly 16 is operated to move the second arm member 14 from the first position to a second position, relative to the first arm member 12 by rotating the second body portion about a joint axis. The connective tissue of the joint is consequently stretched. The orthosis 10 is maintained in the second position for a predetermined treatment time, utilizing the principles of stress relaxation to stretch the connective tissue of the joint. As explained above, previous orthoses may allow the tissue to partially relax as the tissue stretches because the devices simply held the body members in a fixed position. In contrast, the present invention further utilizes a force application assembly 18 to apply loading or forces to the second body portion. This application of force prevents a relaxation of the connective tissue of the joint, utilizing the principles of creep to further stretch the connective tissue of the joint. After the expiration of the treatment time, the second arm member 14 may be returned to the first position, relieving the joint. While in one embodiment, the loading or forces applied are substantially constant, they also may gradually increase, decrease, pulse between a first and second amount of force, or be varied in other ways such as described in the examples and embodiments provided herein.

Optionally, the second arm member 14 can be rotated to a third position, further increasing the stretch of the connective tissue of the joint. The second arm member 14 can be rotated at discrete time intervals to incrementally increase the stretch of the joint through the treatment cycle. In each of the movements, the force application assembly 18 provides the substantially constant force to the second body portion, preventing a relaxation of the connective tissue of the joint. After completion of the treatment cycle, the second arm member 14 is returned to the first position relieving the joint.

Figure 2A:
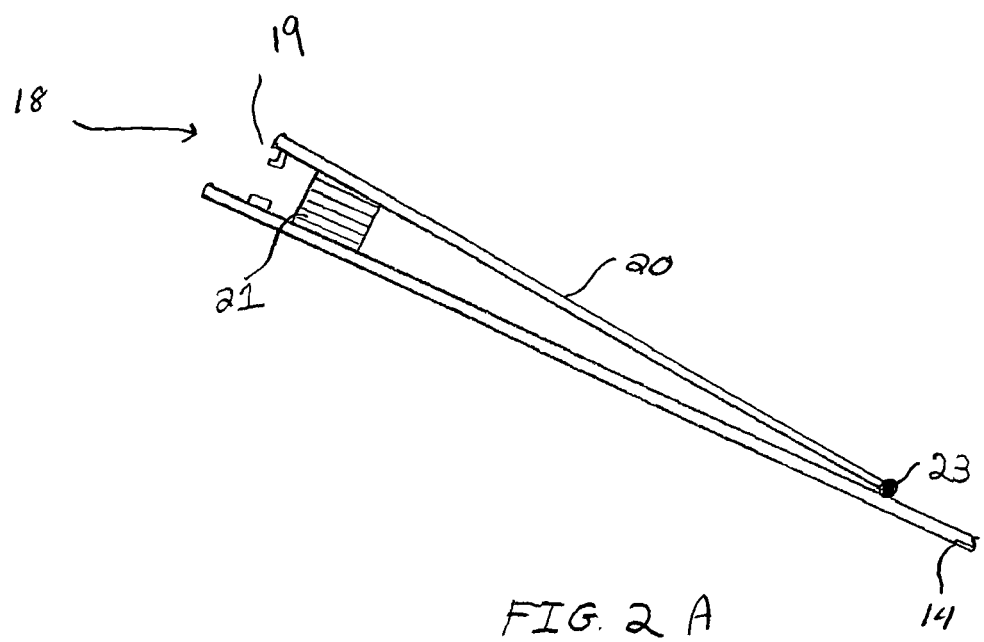
FIG. 2A is a schematic diagram of a force application assembly of the orthosis of FIG. 1.

Referring to FIG. 2A, there is provided a force application assembly 18 of the present invention. The force application assembly 18 includes an assembly member 20 pivotally connected to the second arm member 14, such that the assembly member 20 is interposed between the second arm member 14 and the second body portion. One or more force elements 21, such as a spring, is interposed between the second arm member 14 and the assembly member 20, where the force element 21 provides a force urging the assembly member 20 away from the second arm member 14.

The force application assembly 18 can include a lock out element 19. When engaged, the lock out element 19 secures the assembly member 20 to the second arm member 14, preventing expansion of the force element 21. The lock out element 19 permits the optional use of the force element 21 during the protocol or for any position of the device.

Figure 2B:
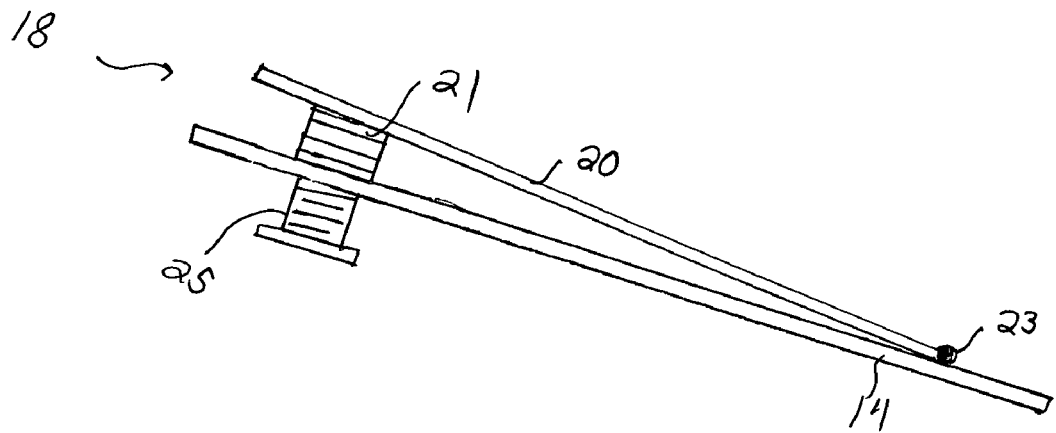
FIG. 2B is a schematic diagram of an adjustable force application assembly of the orthosis of FIG. 1

Referring to FIG. 2B, force application assembly 18 can be adjustable, wherein the force applied by the force element 21 can be controlled. The force application assembly 18 can include a threaded member 25 operably connected to the force element 21. The threaded member 25 can be used to selectively increase or decrease the force applied by the force element 21.

Figure 2C:
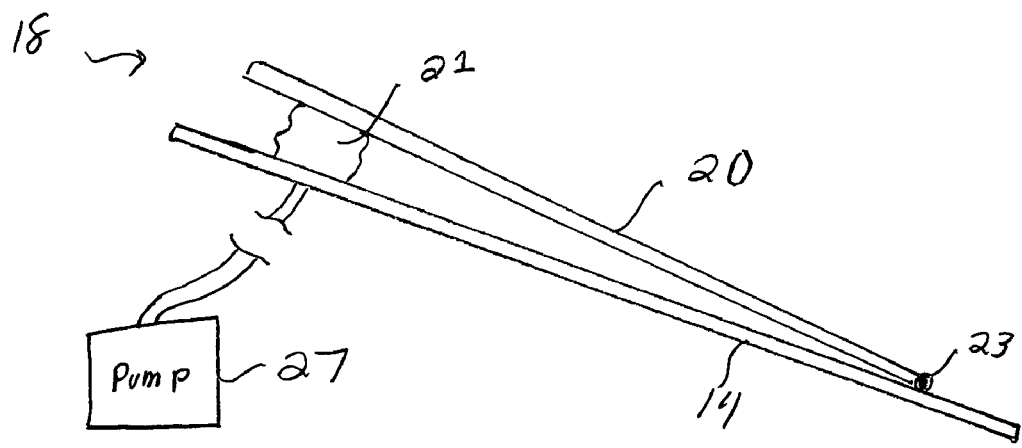
FIG. 2C is a schematic diagram of another adjustable force application assembly of the orthosis of FIG. 1
Figure 3A:
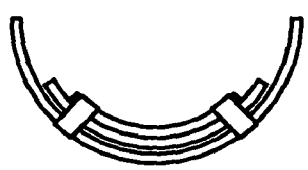
FIGS. 3A-3F depict alternative force elements for use in the force application assembly of FIG. 2A.
Figure 3B:
Figure 3C:
Figure 3D:
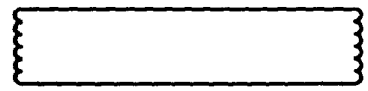
Figure 3E:
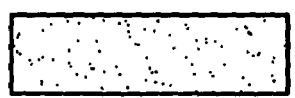
Figure 3F:

Other devices may be used in place of the threaded member 25 to vary the force applied by force element 21. For example, a motor, pressurized bladder, piston, hydraulic or pneumatic system, or other device may be used to vary the force applied. Referring to FIG. 2C, for example, the adjustable force application assembly 18 can include a bladder force element 21. The bladder force element 21 is connected to a pump 27, where the pump can inflate and deflate the bladder force element 21 to selectively increase or decrease the force applied by the bladder force element 21.

While the force element 21 is representative of one or more springs, it should be understood that the force application assembly 18 can use other devices to impart forces on the assembly member 20. It is contemplated that the force elements 21 may be any device that can impart forces urging the assembly member 20 to move relative to the second arm member 14. For instance, referring to FIGS. 3A-3F, the force element can be a leaf spring, a "C" spring, a fluid bladder, and elastic resilient material, or any other related device known in the art. Additional, non-limiting examples of force elements include pneumatic or hydraulic systems, open cell or closed cell foams, and elastic materials such as rubber, urethanes, plastics, or the like. The force element can further include an adjustable force element to increase or decrease the provide force.

Figure 4:
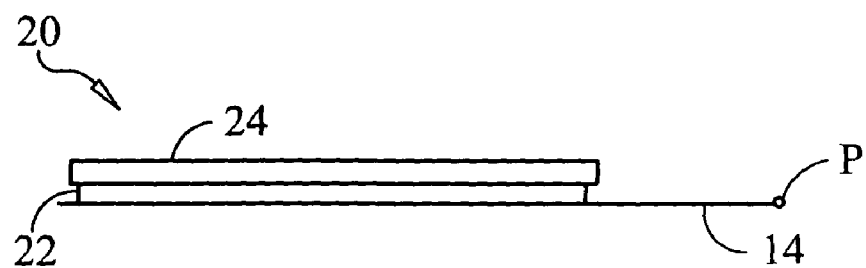
FIG. 4 depicts another force application assembly of the orthosis of FIG. 1.
Figure 5A:
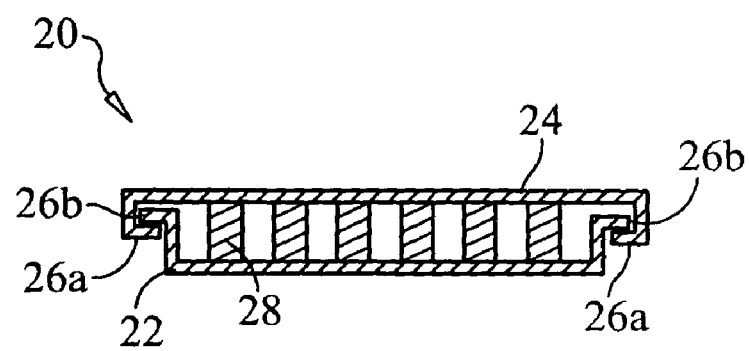
FIG. 5A depicts a sectional view of the force application assembly of FIG. 4.

FIGS. 4 and 5A illustrate an alternative force application assembly 18 of the invention. The force application assembly 18 includes first assembly member 22 connected to the second arm member 14 and a second assembly member 24 slidably positioned over the first assembly member 22. The first and second assembly members 22 and 24 each include lip portions 26a and 26b, limiting the range of motion of the second assembly member 24 with respect to the first assembly member 22. Lip portions 26a and 26b also may help prevent inadvertent removal of the second assembly member 24 from the first assembly member 22. Force elements 28 may be disposed between the first and second assembly members 22 and 24 in order to provide a force urging the second assembly member 24 away from the first assembly member 22.

The force applied to the second assembly member 24 with respect to the first assembly member 22 can be selected based on the therapeutic requirements of a patient. For example, the force elements 30 can be selected to provide a desired force, i.e., 1 lb., 2 lbs., 3 lbs., etc.

In one embodiment, the force applied remains substantially constant during a treatment interval, which, for purposes of this application, is the time during which the device is in use and in a particular configuration or position. Thus, the number of treatment intervals may correspond to the number of different positions or device configurations used in the overall treatment protocol.

The force applied in one treatment interval may differ in degree, profile, or duration of force applied in another treatment interval, although in some cases the applied force may be substantially the same for two or more, or even for all treatment intervals.

The degree of force applied, for example, may be varied from one treatment interval to another, and likewise the degree of force applied may be adjusted depending upon different factors or patient needs. Force elements 28, for example, may comprise one or more spring elements that, when compressed, impart an outward force on the first and second assembly members. The force elements and assembly members may be configured so that the force members are always partially compressed or deformed, thereby creating a pre-load force that must be overcome in order to move the assembly members closer together. The amount of initial deflection, and therefore the amount of preloading of the force elements, may be made adjustable by providing a movable plate, washer, screw, or other force adjustment device disposed at least partially between the assembly members.

If a plurality of force members are used, such as by providing several springs distributed along the area of the interior surfaces of the assembly members, more than one force adjustment devices may be used in order to allow even greater control and variation of the forces applied during a treatment interval. For instance, it may be desirable to provide a different degree of force in one region than in another.

Figure 15A:
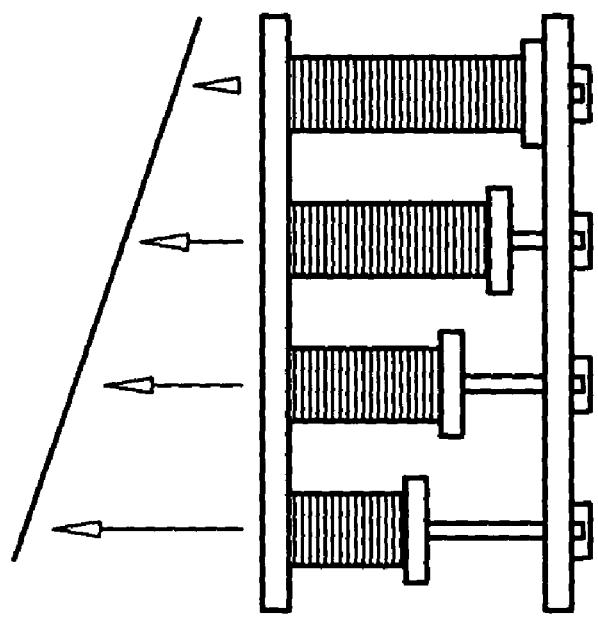
FIGS. 15A and 15B depict examples of force profiles that can be applied by the force application assembly FIG. 16 depict another orthosis of the present invention.
Figure 15B:
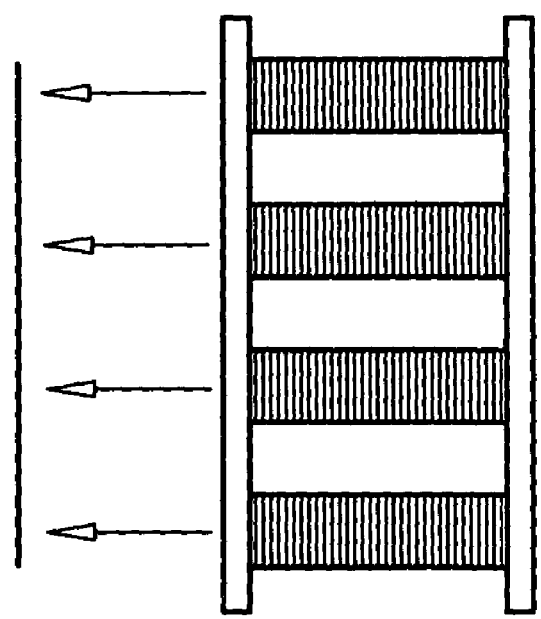

Thus, while in some cases it may be desirable to have a relatively uniform force profile as illustrated in FIG. 15A, it may also be desirable to apply a greater force on one end, side, or region of the device than another, as shown in FIG. 15B. Additionally, there may be circumstances when it is desirable to apply little, if any, force in one region of the device. For example, the patient may have an injury in part of the treated anatomy, such as bruising, scarring, cuts, stitches, or the like that is sensitive to application of pressure forces.

The adjustment devices may be configured to permit access and adjustment of the force preload and/or profile during a treatment protocol. In this manner, a physician may be able to assess and adjust the imparted forces for any treatment interval.

Additionally, adjustments also may be made during a treatment interval. For example, adjustments may be made during a treatment interval in order to increase or decrease the forces imparted, even though the geometric angle or position of the device remains unchanged. In one example, the initial force imparted at the beginning of a treatment interval may be low, but then increased over time according to a patient's progress or according to a predetermined time schedule. In another example, it may be desirable to initially apply a greater force in order to help accelerate a patient's progress, but then later relieve or reduce the forces applied after achieving a satisfactory degree of stretching or after a predetermined time.

In addition, the force application assembly 18 can include a force control system for control the force applied by the force elements 30. A pneumatic or hydraulic system, for example, may have controls for the amount of force imparted by any or all of the force elements as well as the force profile and direction of applied forces. Likewise, a servo-mechanical force control system may be used to vary the amount of deflection or preload of spring-like force elements.

Moreover, while the examples and descriptions provided herein illustrate how the invention may be used to treat flexion and extension contractures, the concepts may also be applied to treating contractures limiting rotational range of motion. Thus, the devices described herein also may be configured to increase the rotational range of motion, such as supination or pronation, for a joint in addition to, or instead of, treating bending. For example, a device for treating contractures in a shoulder, elbow, wrist, hip or ankle joint may be configured to help enhance rotational capability of the joint.

Figure 5B:
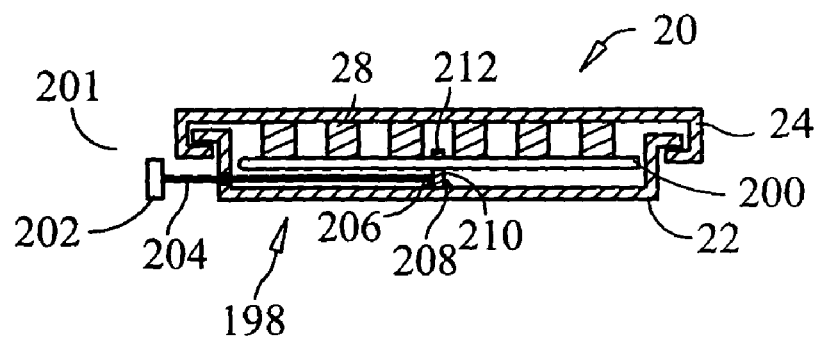
FIG. 5B depicts sectional view of the force application assembly including a force control system.

Referring to FIG. 5B, the force application assembly 18 includes a force control system 198 having a first assembly member 22 connected to the second arm member 14 and a second assembly member 24 slidably positioned over the first assembly member 22. A compression plate 200 is positioned within the second assembly member 24, where the force elements 28 are disposed between the compression plate 200 and the first assembly member 22. A drive mechanism 201 is provided to raise and lower the compression plate 200, compressing or extending the force elements 30 to selectively increase or decrease the substantially constant force.

The drive mechanism 201 may include a knob 202 connected to a shaft 204, the opposite end of the shaft 204 including a worm drive 206. The knob 202, shaft 204, and worm drive 206 are connected such that a rotation of the knob 202 rotates the worm drive 206. A threaded member 208 is rotatably mounted to the second assembly member 24 and includes a gear 210 for engaging the worm drive 206. The gear 210 engages the worm drive 206 such that a rotation of the worm drive 206 results in a rotation of the threaded member 208. The threaded member 208 is positioned and threaded through a threaded aperture 212 in the compression plated 200, such that as the threaded member 208 is rotated the compression plate 200 is raised or lowered. In this manner the force elements 30 can be compressed or expanded to selectively change the substantially constant force.

In the previous examples, the force application assembly 18 is disclosed as being interposed between the second arm member 18 and the second body portion, providing a force to the second body portion. However, it is contemplated that the force application assembly 18 can be in other locations or positions, such as adjacent to the drive assembly 16. Likewise, the force application assembly 18 can include a torsional spring position about the joint axis and interposed between the first and second arm members 12 and 14. The torsional spring can provide a force to the second arm member 14 with respect to the first arm member 12, utilizing the principles of creep to further stretch the connective tissue of the joint. Alternatively, the force application assembly 16 can be integrated into the drive assembly.

Figure 6:
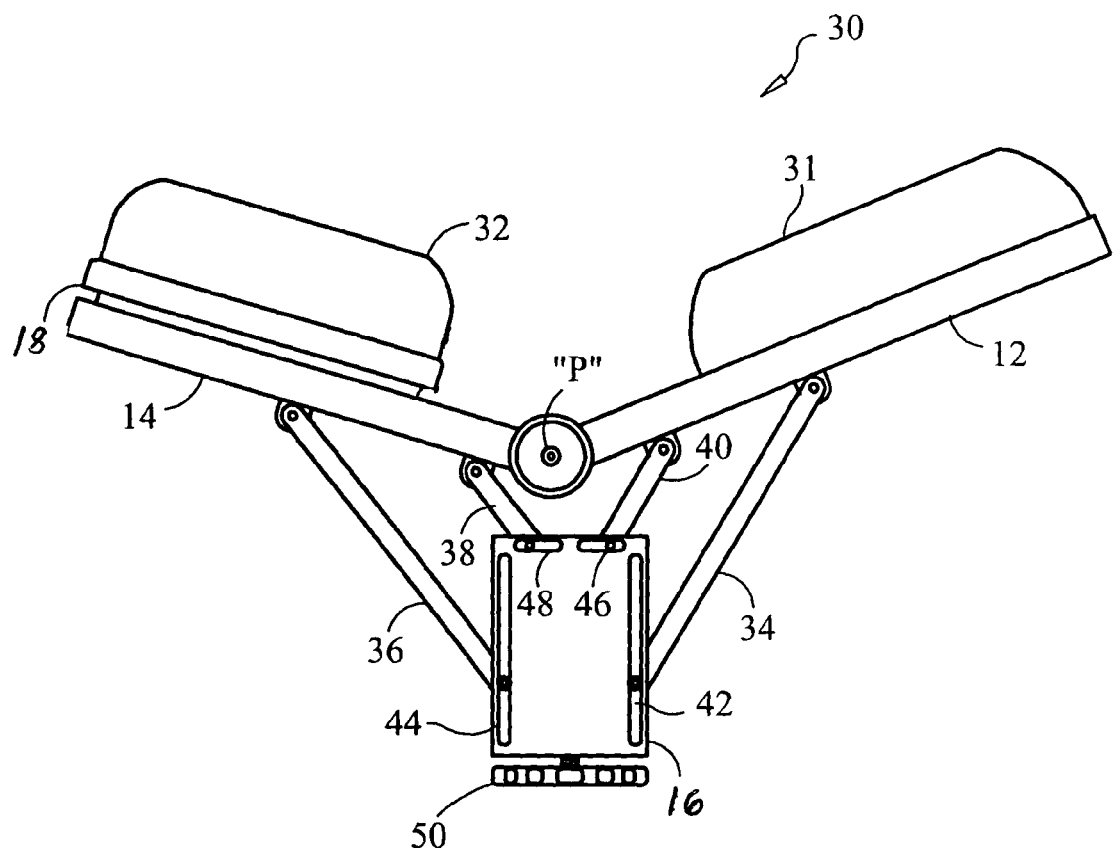
FIG. 6 depicts an exemplary orthosis.

Referring to FIG. 6, there is shown an orthosis 30 of the present invention. The orthosis 30 includes first and second arm members 12 and 14 pivotally connected at "P." The first arm member 12 includes a first cuff 31 for attachment to the first body portion. (The term "cuff" as used herein means any suitable structure for transmitting the force of the orthosis to the limb portion it engages.) The second arm member 14 includes the force application assembly 18 and a second cuff 32, for attachment to the second body portion, wherein the force application assembly 18 is interposed between the second cuff 32 and the second arm 14, such that the force application assembly 18 can provide the substantially constant force to the second body portion. The cuffs 31 and 32 can include a strap, such as VELCRO straps and foam portions to secure the cuffs 31 and 32 to the body portions.

The drive assembly 16 is operably connected to the first and second arm members 12 and 14. The drive assembly 16 includes first and second lever arms 34 and 36 pivotally connected to the first and second arm members 12 and 14 and operably connected to a drive mechanism of the drive assembly 16. Operation of the drive mechanism actuates the lever arms 34 and 36 to move the first and second arm members 12 and 14. Tracking arms 38 and 40 are pivotally connected to the first and second arm members 12 and 14 and slidably connected to the drive assembly 16, stabilizing the drive assembly 16 with respect to the first and second arm member 12 and 14.

Figure 7:
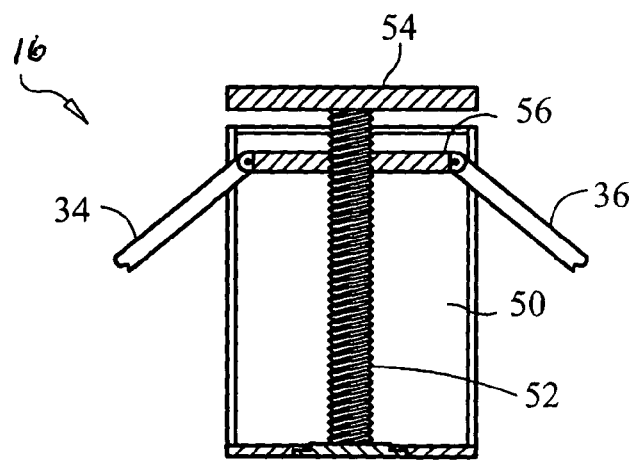
FIG. 7 depicts a drive mechanism of the orthosis of FIG. 6.

Referring to FIG. 7, a drive mechanism 50 of the drive assembly 16 is provided. The drive mechanism 50 includes a worm 52 rotatably mounted within the drive assembly 16. A knob 54 is connected to the worm 52, such that a rotation of the knob 54 rotates the worm 52. A threaded actuation sleeve 56 is position on the worm 52, such that as the worm 52 is rotated the threaded sleeve traverses the worm 52. The first and second lever arms 34 and 36 are pivotally connected to the threaded sleeve 54. In operation a rotation of the knob 56 results in an actuation of the lever arms 34 and 36, moving the first and second arm members 12 and 14.

In an alternative embodiment, the drive assembly 16 for an orthosis 10 in accordance with the present invention can be actuated by a motor instead of by a manually actuatable member, such as the knob 54.

In one embodiment, an electric motor is mounted to the worm 52. A battery may provide electric power to the motor, or it may be powered from another source. A microprocessor can be used to operate the motor to more accurately control positioning of the arm members or to allow for automation of some steps of treatment such as moving from one position to another. The motor may also operate within a control system that allows for remote operation of the device by a healthcare professional or technician. The microprocessor and motor together can be used to cycle the first and second arm members 12 and 14 through extension and flexion (or rotational positions); to move the first and second arm members 12 and 14 in one pivotal direction a certain amount, hold there while tissue stretches, then move further in that direction; or in any other manner. In another manner of use, the orthosis can be set to cycle to one end of the joint's range of motion and hold there for a predetermined period of time, then cycle to the other end of the joint's range of motion and hold there. Given the benefit of this disclosure, skilled artisans would understand how to program and control the microprocessor so that the first and second arm members 12 and 14 move as desired. This embodiment is ideally suited for continuous passive motion exercise, because it can be programmed with the desired sequence of movements. Preferably, at least this embodiment of the invention also would be a portable device so that it may be provided to a patient to use in the home, at work, or wherever they may desire.

It should be understood that the particular physical arrangement of the motor, the battery, and the microprocessor is not the only possible arrangement of those elements. The invention contemplates that other arrangements of these or similarly functional elements are quite suitable, and thus, the invention is intended to cover any such arrangement. Additionally, another type of actuation, other than an electric motor, can also be used. For example, the use of a hydraulic or pneumatic motor as the drive mechanism is contemplated.

Figure 8:
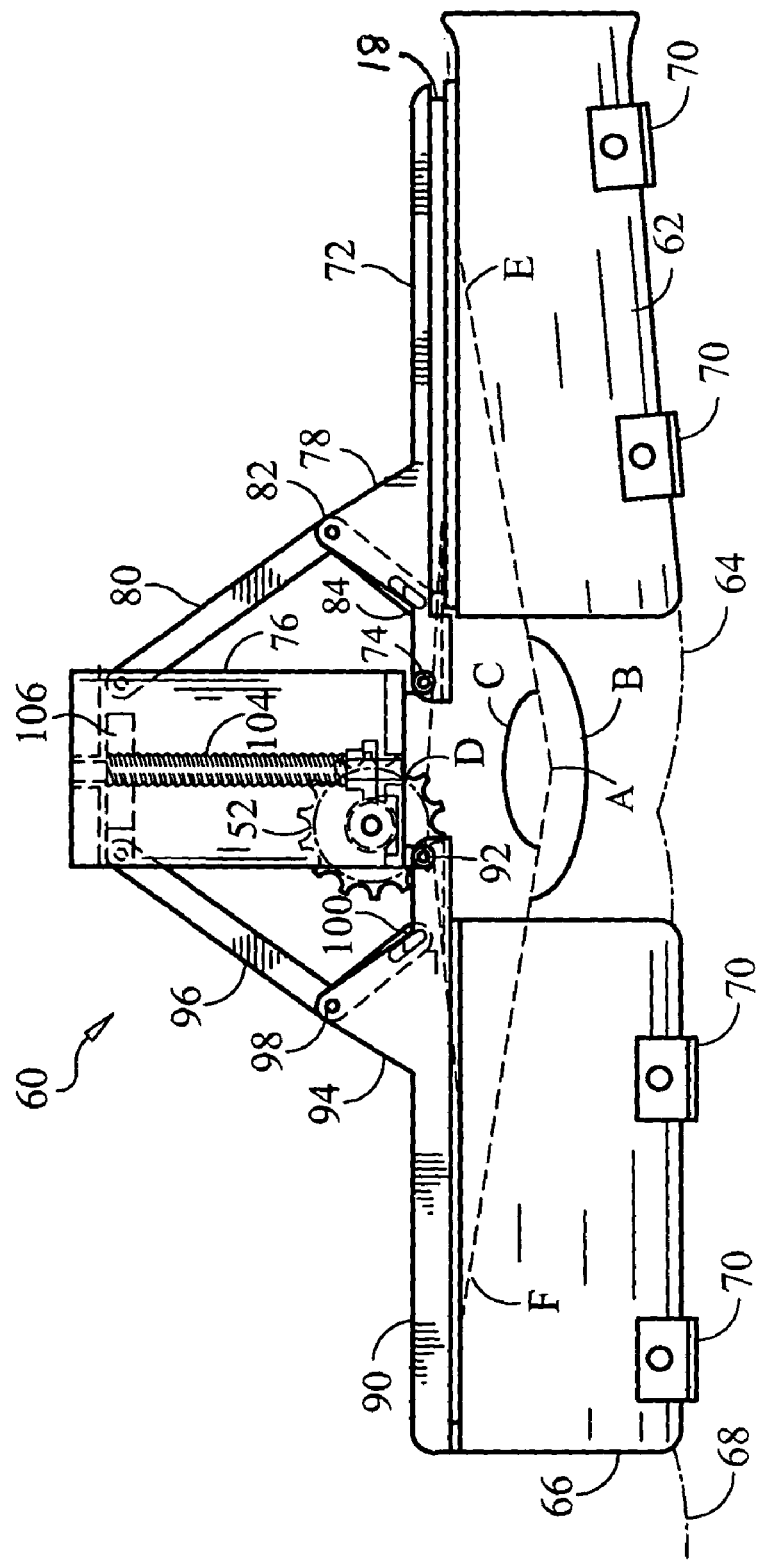
FIG. 8 depicts another exemplary orthosis.

The present invention can further include a monitor for use with the device 10, which provides assurances the patient is properly using the device 16 during his/her exercise period. For instance, the monitor can have a position sensor, a temperature sensor, a clock or timer, or a device type sensor for monitoring the patient's implementation of a protocol. The information obtained from these monitoring devices may be stored for later analysis or confirmation of proper use or may be transmitted in real-time during use of the device. The data obtained from the monitor can be analyzed by a healthcare professional or technician and the protocol can be adjusted accordingly. This analysis may be conducted remotely, thereby saving the time and expense of a home visit by a healthcare professional or technician. An exemplary monitoring system is provided in U.S. Publication No. 20040215111 entitled "Patient Monitoring Apparatus and Method for Orthosis and Other Devices," to Bonutti et al., the content of which is herein expressly incorporated by reference in its entirety Referring to FIG. 8, another orthosis 60 of the present invention is provided. The orthosis 60 includes a second cuff 62 for attachment to a second body portion 64 such as the forearm, and a first cuff 66 for attachment to a first body portion 68 such as the upper arm. The second body portion 64 is joined to the first body portion 68 at the elbow joint designated A, around which is located, as is well known, soft tissue. Each of the first and second cuffs 66 and 62 includes a plurality of loop connectors 70 for receiving straps extending around the body portions 68 and 64 to clamp the cuffs 66 and 62 to the body portions 64 and 68. The second cuff 62 is mounted onto a second cuff arm 72, wherein a force application assembly 18 is interposed between the second cuff 62 and the second cuff arm 72, such that the force application assembly 18 can provide a constant force to the second body portion 64.

The second cuff arm 72 is pivotally mounted by a pin 74 to a drive assembly 76. The second cuff arm 72 includes a support 78. A first lever arm 80 extends from the drive assembly 76 and is pivotally connected to the support 78 by a pin 82. The first lever arm 80 is pivotally connected to a cuff actuator block 84. The cuff actuator block 34 is fixed to the second cuff 62.

The first cuff 66 is mounted on a first cuff arm 90. The first cuff arm 90 is pivotally mounted by a pin 92 to the drive assembly 76. The first cuff arm 90 includes a support 94. A second lever arm 96 extends from the drive assembly 76 and is pivotally connected to the support 94 by a pin 98. The second lever arm 96 is pivotally connected to a cuff actuator block 100. The cuff actuator block 100 is fixed to the second cuff 16.

The drive assembly 76 includes a drive mechanism having a manually actuatable knob 102 operably connected to a threaded shaft (worm) 104. The shaft 104 extends through the drive assembly 76. A threaded actuator block 106 is threaded on the shaft 104, wherein the first and second lever arms 80 and 96 are pivotally connected to the actuator block 106.

The knob 102 is turned so that the arm actuator block 106 moves, either upward or downward. As the actuator block 106 moves it applies a directed force to the first lever arm 80. This force is transmitted to the support 78 and to the second cuff arm 72. The second cuff arm 72 pivots about the pin 74.

Operation with respect to the first cuff arm 90 is similar. As the actuator block 106 moves it applies a directed force on the second lever arm 96. This force is transmitted to the first cuff arm 90. The first cuff arm 90 pivots about the pin 92 relative to the drive assembly 76.

Figure 9:
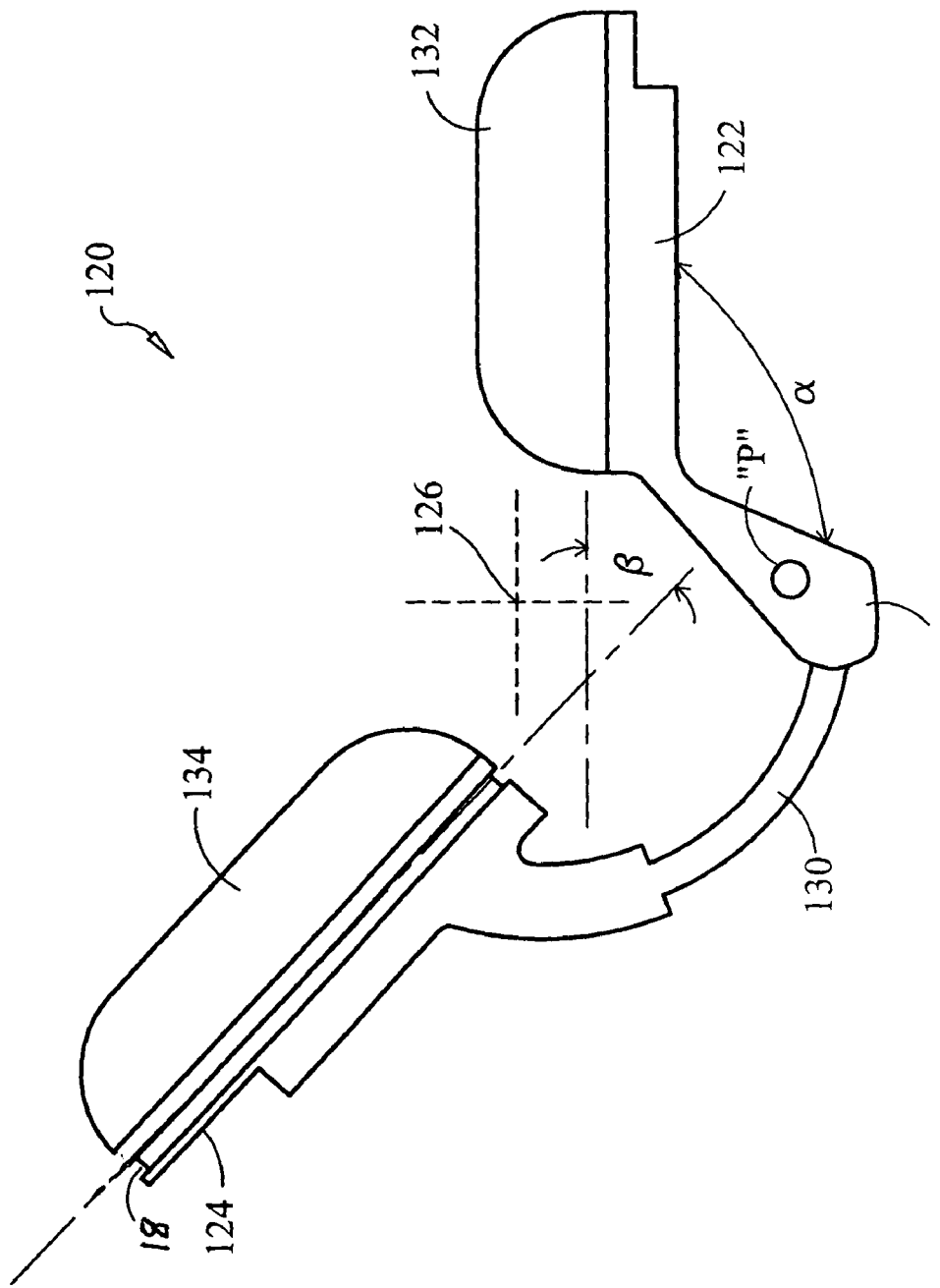
FIG. 9 depicts a further exemplary orthosis.

Referring to FIG. 9, an orthosis 120 of the present invention includes a first arm member 122 attachable to the first body portion and a second arm member 124 attachable to the second body portion, wherein the joint axis 126 is interposed between and offset from the first and second arm members 122 and 124. The first and second arm members 122 and 124 are connected with each other offset from the joint axis 126.

The first arm member 122 of the orthosis 120 includes a first extension member 128, which extends at angle α from the first arm member 122. The second arm member 124 of the orthosis 120 includes a second extension member 130, having an arcuate shape. The first and second extension members 128 and 130 are operatively connected a point "P," such that in operation the second extension member 130 travels along an arcuate path about and substantially through point "P." The arcuate shape of the second extension member 130 results in the second body portion rotating about axis 126, which preferably corresponds to the joint axis, when the second arm member 124 is moved from a first position to a second position relative to the first arm member 122. The angle β between the longitudinal axis of the first arm member 122 and the longitudinal axis of the second arm member 124 is a function of the joint to be treated and the degree of flexion or extension contractures.

A first cuff 132 is attached to the first arm member 122, wherein the first cuff 132 is positionable about the first body portion. The first cuff 132 is attached to the first body portion by cuff straps. The first cuff 132 secures the first body portion to the first arm member 122. A second cuff 134 is attached to the second arm member 124, wherein a force application assembly 18 is interposed between the second arm member 124 and the second cuff 134. The second cuff 134 is positionable about the second body portion and is attached to the second body portion by cuff straps, such that the force application assembly 18 can provide a constant force to the second body portion.

Figure 10:
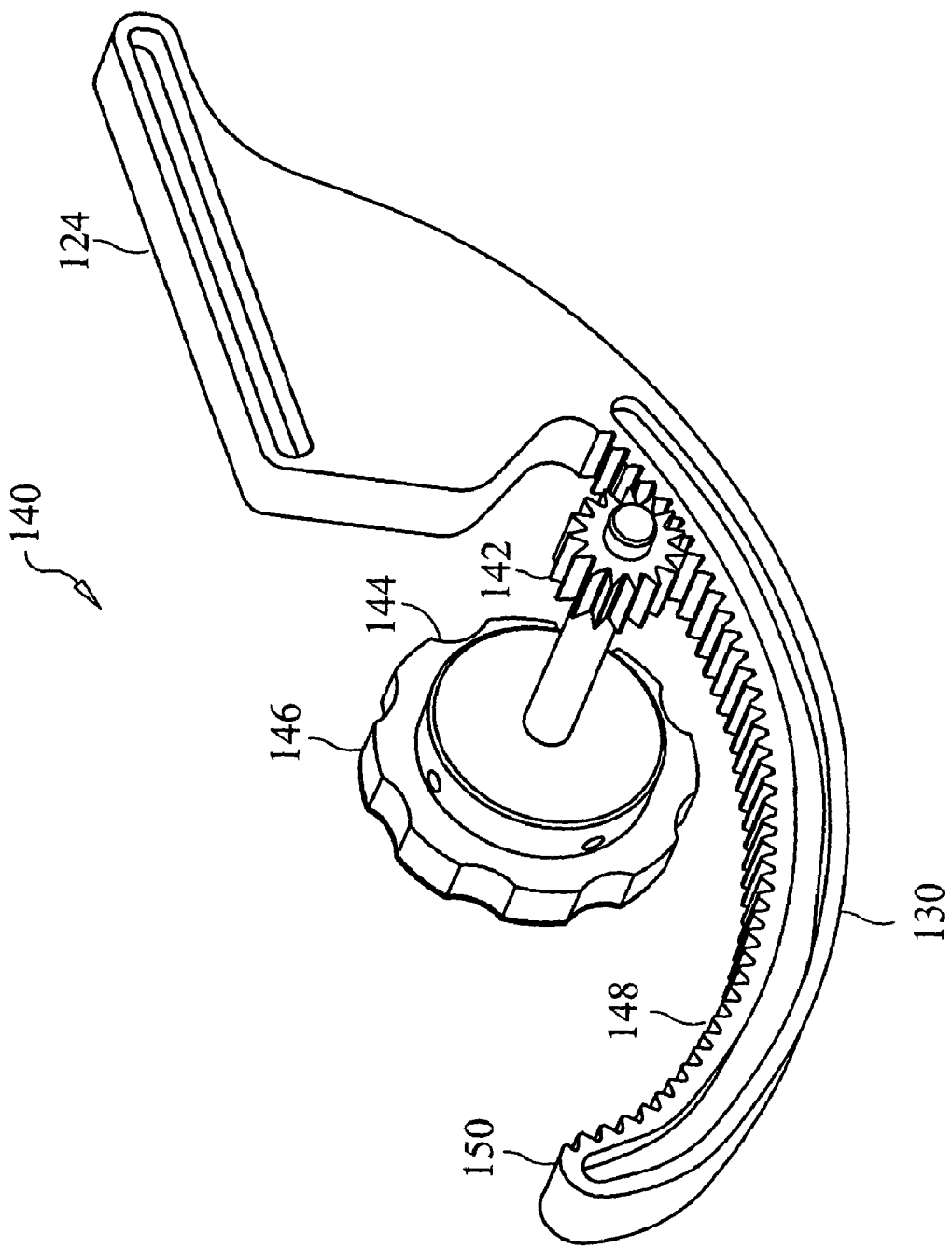
FIG. 10 depicts a drive assembly of the orthosis of FIG. 9.

Referring to FIG. 10, the drive assembly 140 of the orthosis 120 includes a gear system. The drive assembly 140 is supported in the first extension member 128 including a gear 142 rotatable about point "P." A shaft 144, attached to the gear 142, extends from first extension member 128. A knob 146 is connected to the shaft 144, opposite the gear 142, for manually rotating the gear 142. The second extension member 130 includes a series of teeth 148 along an inner surface 150. The second extension member 130 is threaded through the first extension member 128, such that the teeth 148 on the second extension member 130 engage the gear 142. The rotation of the knob 146 causes the gear 142 to rotate, pushing or pulling the second extension member 130 through the first extension member 128. The drive assembly 140 includes a locking or breaking mechanism which prevents the gear 142 from rotating absent an applied force rotation of the knob 146. Such a lock or breaking mechanism can include a compression washer or other known gear locking or breaking mechanisms.

The drive assembly 140 is described as utilizing a gear system. However, it is contemplated that other known drive systems can be used to move the second extension member 130 through the first extension member 128, for example a friction type drive system. Regardless of the drive system used, the joint orthosis of the present invention can act as a brace, restricting the relative movement of the first and second body portions to one degree of freedom (e.g. flexion and extension about the joint). Thus, drive assembly 140 can be configured to allow free motion in one degree of freedom. This can be achieved in a number of different ways. For example, gear 142 can be positioned such that it does not engage teeth 148.

In an alternative embodiment, the drive assembly 140 for an orthosis 120 in accordance with the present invention can be actuated by a motor instead of by a manually actuatable member, such as the knob 146, as previously described.

Figure 11:
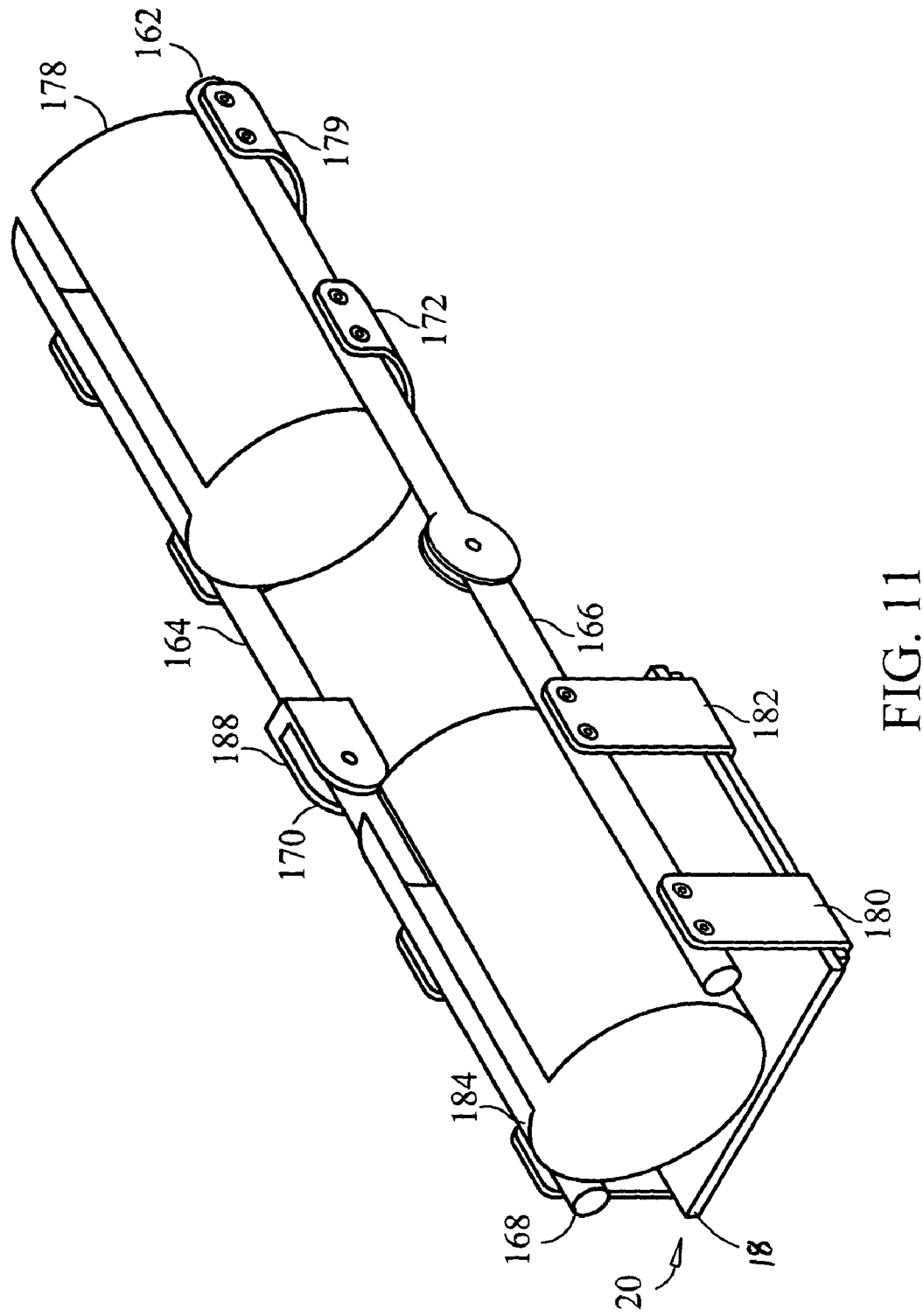
FIG. 11 depicts an isometric view of a still further exemplary orthosis.
Figure 12:
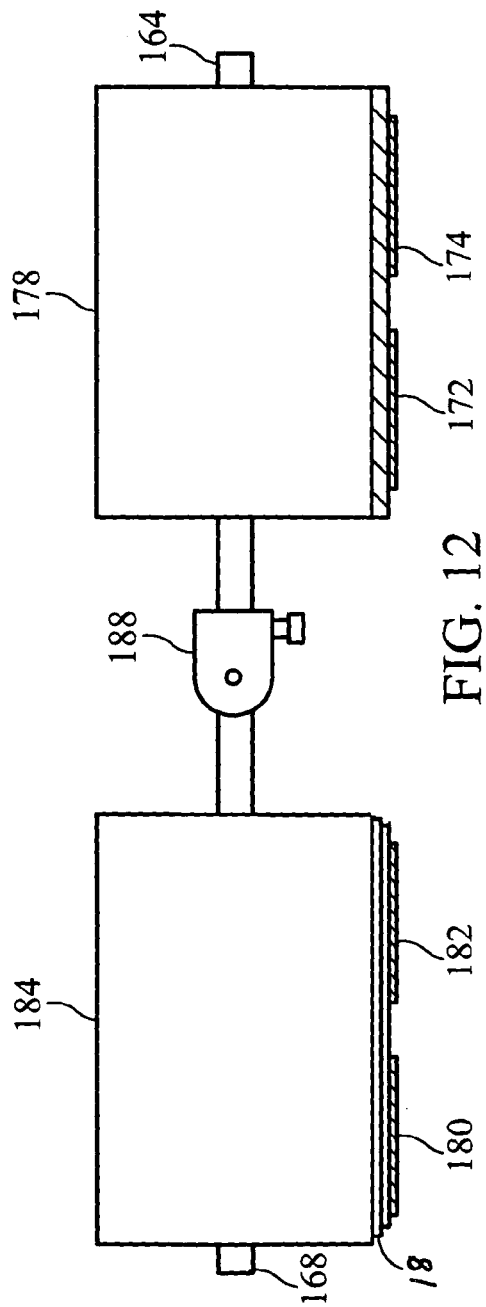
FIG. 12 depicts a partial sectional view of the orthosis of FIG. 11.

Referring to FIGS. 11 and 12, an orthosis 160 of the present invention includes a first pair of arm members 162 and 164 attachable to the first body portion and a second pair of arm members 166 and 168 attachable to the second body portion, wherein the joint axis 170 is interposed between the first and second arm member pairs 162, 164, 166, and 168. The first and second arm member pairs 162, 164, 166, and 168 are pivotally connected with each other on the joint axis 170.

The first pair of arm members 162 and 164 include attachment brackets 172 and 174 attach there to. A first cuff 178 is attached to the attachment brackets 172 and 174, wherein the first cuff 178 is positionable about the first body portion. The first cuff 178 is attached to the first body portion by cuff straps. The first cuff 178 secures the first body portion to the first pair of arm members 162 and 164.

The second pair of arm members 166 and 169 include attachment brackets 180 and 182 attach there to. A second cuff 184 is attached to the attachment brackets 180 and 182, wherein a force application assembly 18 is interposed between the attachment brackets 180 and 182 and the second cuff 184. The second cuff 184 is positionable about the second body portion and is attached to the second body portion by cuff straps, such that the force application assembly 18 can provide a constant force to the second body portion.

Figure 13:
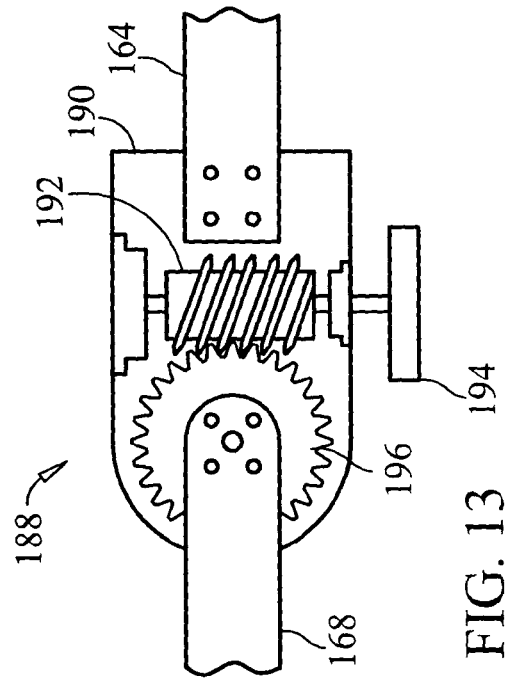
FIG. 13 depicts a sectional view of a drive assembly of the orthosis of FIG. 11.

A drive assembly 188 is connected to and interposed between the first arm member 164 and the second arm member 168. As shown in FIG. 13, the drive assembly 188 includes a housing 190 connected to first arm member 164. The housing 190 includes a worm 192 mounted therein and operably connected to a knob 194. A rotation of the knob 194 rotates the worm 192. A main gear 196 is rotatably mounted to the housing 190, where the main gear 196 rotates about the joint axis 170. The main gear 196 is mounted in engagement with the worm 194, such that as the worm 194 is rotated the main gear 196 is rotated. Second arm member 168 is affixed to the main gear 196, such that as the main gear 196 is rotated the second arm member 168 is rotated about the joint axis with respect to the first arm member 164, In an alternative embodiment, the drive assembly 188 for an orthosis 160 in accordance with the present invention can be actuated by a motor instead of by a manually actuatable member, such as the knob 194.

Additionally, when a joint is flexed or extended a compressive force may be applied to the connective tissue surrounding the joint. It may be desirable to control the compressive force, distracting the joint as the joint is flexed or extended. "Distraction" is defined by one dictionary as "Separation of the surfaces of a joint by extension without injury or dislocation of the parts." (Taber's Cyclopedic Medical Dictionary, 16th Edition, 1989, page 521), and involves stretching rather than compressing the joint capsule, soft tissue, ligaments, and tendons.

Referring again to FIG. 6, the orthosis 30 includes two relatively pivotable arm members 12 and 14. Each arm member 12 and 14 includes a cuff 31 and 32 mounted there to, where the first cuff 31 is slidably mounted to the first arm member 12 and the second cuff 32 is slidably mounted to the force application assembly 18. The cuffs 31 and 32 clamp onto the body portions on either side of the joint. The pivot axis "P" of the arm member 12 and 14 is spaced from the axis of rotation of the joint. Movement of the arm member 12 and 14 to extend the joint may result in distractive forces being applied to the joint. These distractive forces are limited and controlled by having the cuffs 31 and 32 slidable on the arm members 12 and 14. The cuffs 31 and 32 are selectively moved along the arm member 12 and 14, during relative movement of the arm member 12 and 14, to provide the proper amount of distractive forces to the joint and to limit compressive forces on the joint.

Figure 14:
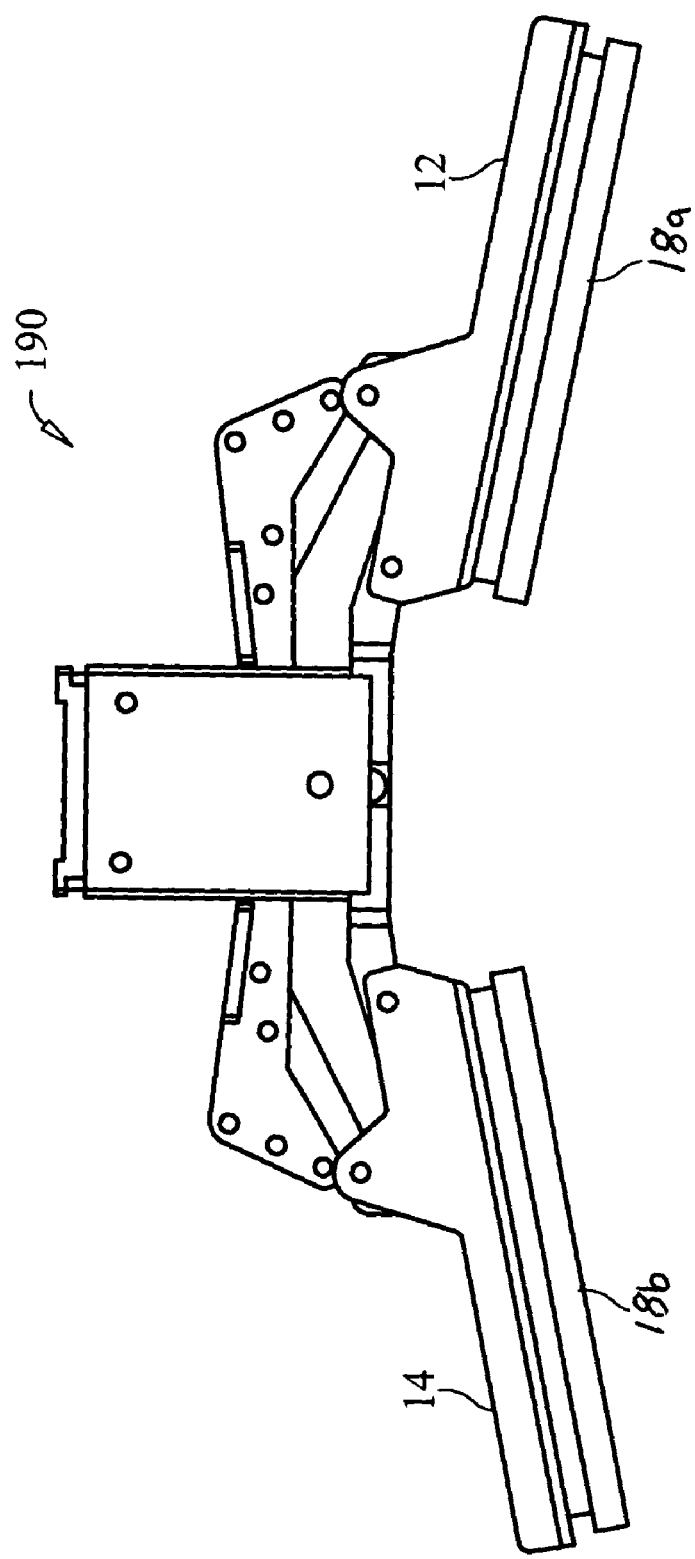
FIG. 14 depicts an orthosis including a pair of force application assemblies.

Referring to FIG. 14, the orthosis 190 includes a first arm member 12 attachable to a first body portion and a second arm member 14 attachable to a second body portion. The orthosis 190 further includes a first force application assembly 18a connected to the first arm member 12. The first force application assembly 18a may be positioned between the first arm member 12 and the first body portion, such that the first force application assembly 18a provides a substantially constant force to the first body portion A second force application assembly 18b connected to the second arm member 14. The second force application assembly 18b may be positioned between the second arm member 14 and the second body portion, such that the second force application assembly 18b provides a substantially constant force to the second body portion.

Figure 16:
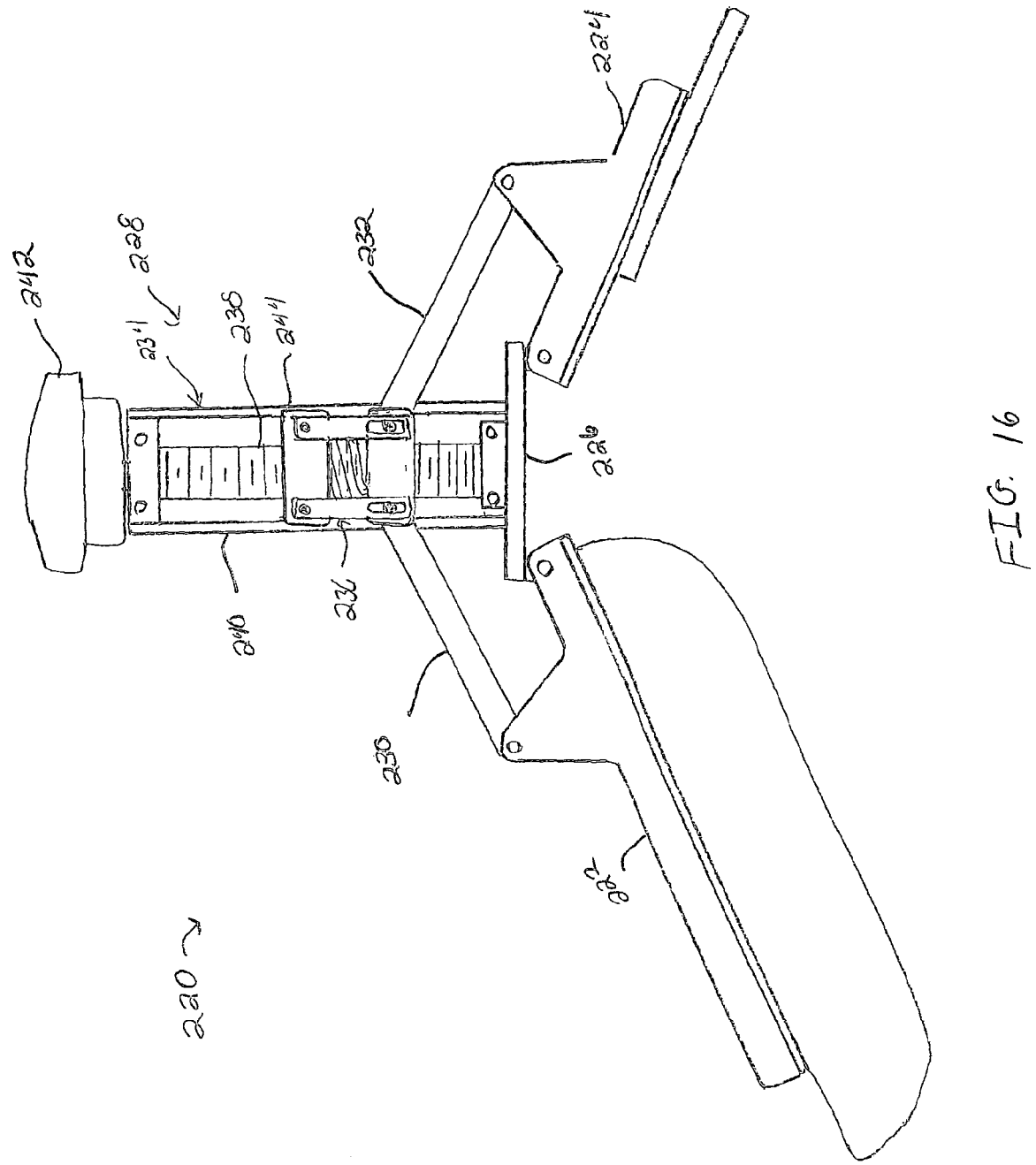

Referring to FIG. 16, another orthosis 220 of the present invention is provided. The orthosis 220 includes first and second arm member 222 and 224 pivotally connected to a base member 226. A control assembly 228 is mounted to the base member 226 proximal to the first and second arm members 222 and 224. The first arm member 222 is operably connected to the control assembly 228 with a first lever arm 230 and the second arm member 224 is operable connected to the control assembly 228 with a second lever arm 232, such that an operation of the control assembly pivots the first and second lever arms 222 and 224 about the base member 226.

The control assembly 228 includes a drive assembly 234 and an integrated force application assembly 236. The drive assembly 234 includes a thread member 238 rotatably mounted in a control frame 240, where a first end of the threaded member 238 in rotatably connected to the base member 226 and a second end of the threaded member 238 is connected to a knob 242, such that a rotation of the knob 242 rotates the threaded member 238. A threaded bushing 244 is slidably mounted in the control frame 240 about the threaded member 238, such that rotation of the threaded member 238 causes the threaded bushing 244 to traverse the threaded member 238.

Figure 17:
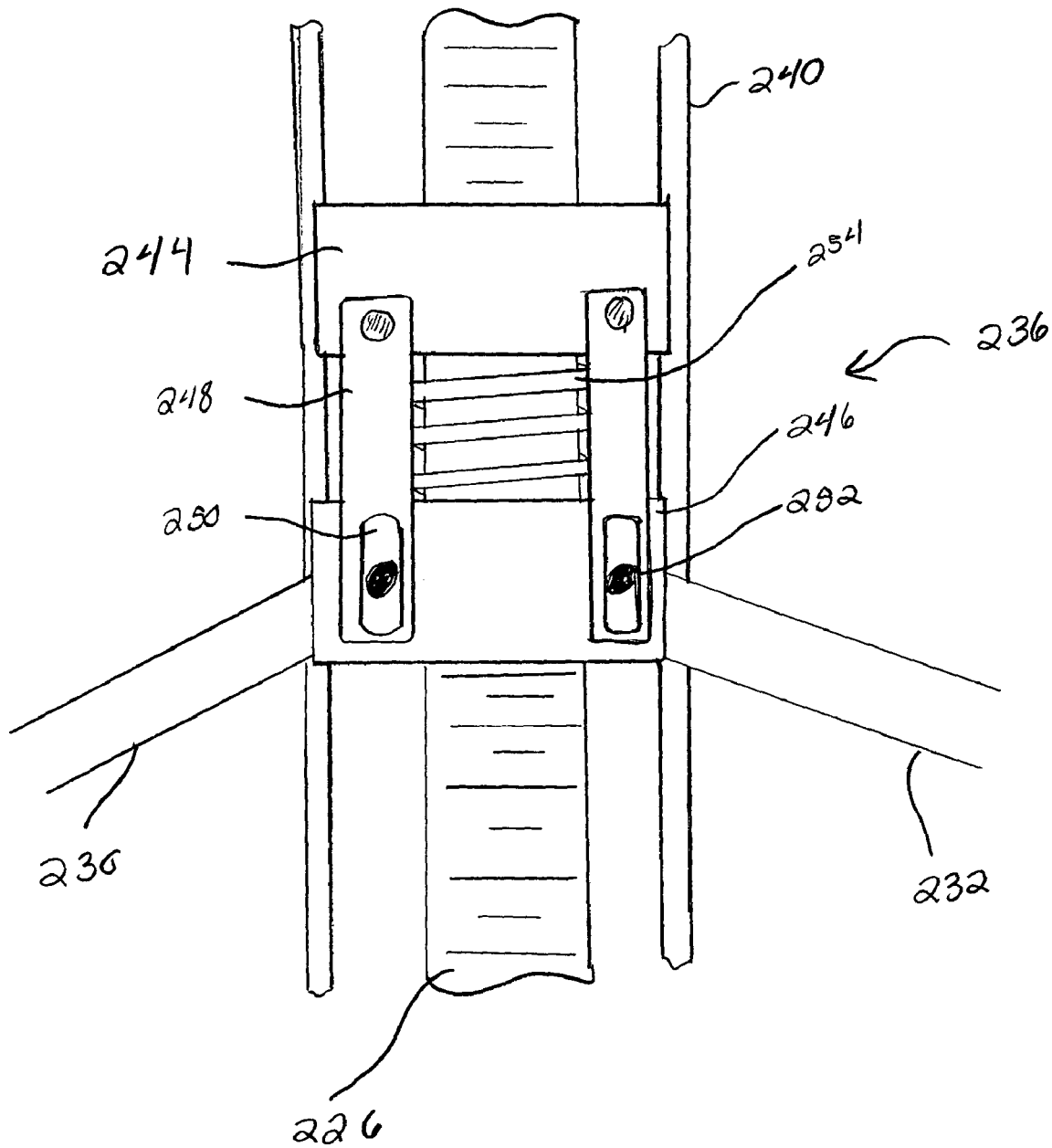
FIG. 17 depicts a control assembly of the orthosis or FIG. 16.

Referring to FIG. 17, the force application assembly 236 is integrated to the drive assembly 234 and includes a slip bushing 246 slidably mounted in the control frame 240 about the threaded member 238. The slip bushing 246 is movably connected to the threaded bushing 244 with elongated connectors 248, where a first end of the elongated connectors 238 are affixed to the threaded busing 244. A second end of the elongated connectors 248 includes slotted portions 250 configured to receive pin members 252 affixed to the slip bushing 246, such that the slip bushing 246 can move with respect to the threaded bushing 244 along the slotted portions 250. The first and second lever arms 230 and 232 are pivotally connected to the slip bushing 246. A force element 254, such as a spring, is interposed between the threaded bushing 244 and the slip bushing 246.

The knob 242 may be turned to rotate the threaded member 226 such that the threaded bushing 244 and the slip bushing 246 move, either upward or downward along the threaded member 226. As the threaded bushing 244 and the slip bushing 246 move, the slip bushing 224 applies a directed force to the first and second lever arms 230 and 232. This force is transmitted to the first and second arm members 222 and 224, pivoting the first and second arm members 222 and 224 with respect to the base member 226.

In an exemplary use, the orthosis 220 is operated to extend a joint in the following manner. The first arm member 22 is fastened to the first body portion and the second arm member 224 is fastened to the second body portion. The orthosis 220 is attached to the first and second body portions in a first position. The drive assembly 234 is operated to move the second arm member 224 from the first position to a second position, relative to the first arm member 222. The connective tissue of the joint is consequently stretched. The orthosis 220 is maintained in the second position for a predetermined treatment time, utilizing the principles of stress relaxation to stretch the connective tissue of the joint.

As explained above, previous orthoses may allow the tissue to relax as the tissue stretches because the devices simply held the body members in a fixed position. In contrast, the present invention further utilizes a force application assembly 236 to apply loading or forces to the second body portion. This application of force prevents a relaxation of the connective tissue of the joint, utilizing the principles of creep to further stretch the connective tissue of the joint.

Initially, the force applied by the force application assembly 236 may be less than a force applied by the drive assembly 234, such that the force element 254 is compressed between the threaded bushing 244 and the slip bushing 246. As the tissue is stretched, however, the tissue relaxes and reduces the degree of resistance imparted to the drive assembly 234. The drive assembly force may decrease to a point where the force application assembly force exceeds the drive assembly force, such that the force element 254 expanded, moving the slip bushing 236 with respect the threaded bushing 244, providing a force to the tissue. In one embodiment, the force application assembly 238 can impart a substantially constant force onto the second body portion. The application of the force application assembly force utilizes the principals of creep to continuous stretch the joint tissue during the set time period, maintain, decreasing, or preventing a relaxation of the tissue.

After a set time period, the drive assembly 234 may be used to move the second arm member 224 with respect to the first arm member 222 from the second position to a third position, incrementally stretching the tissue surrounding the joint. It is contemplated that the drive assembly 234 may be used to incrementally move the second body portion after the expiration of a predetermined time or until completion of the protocol.

Figure 18:
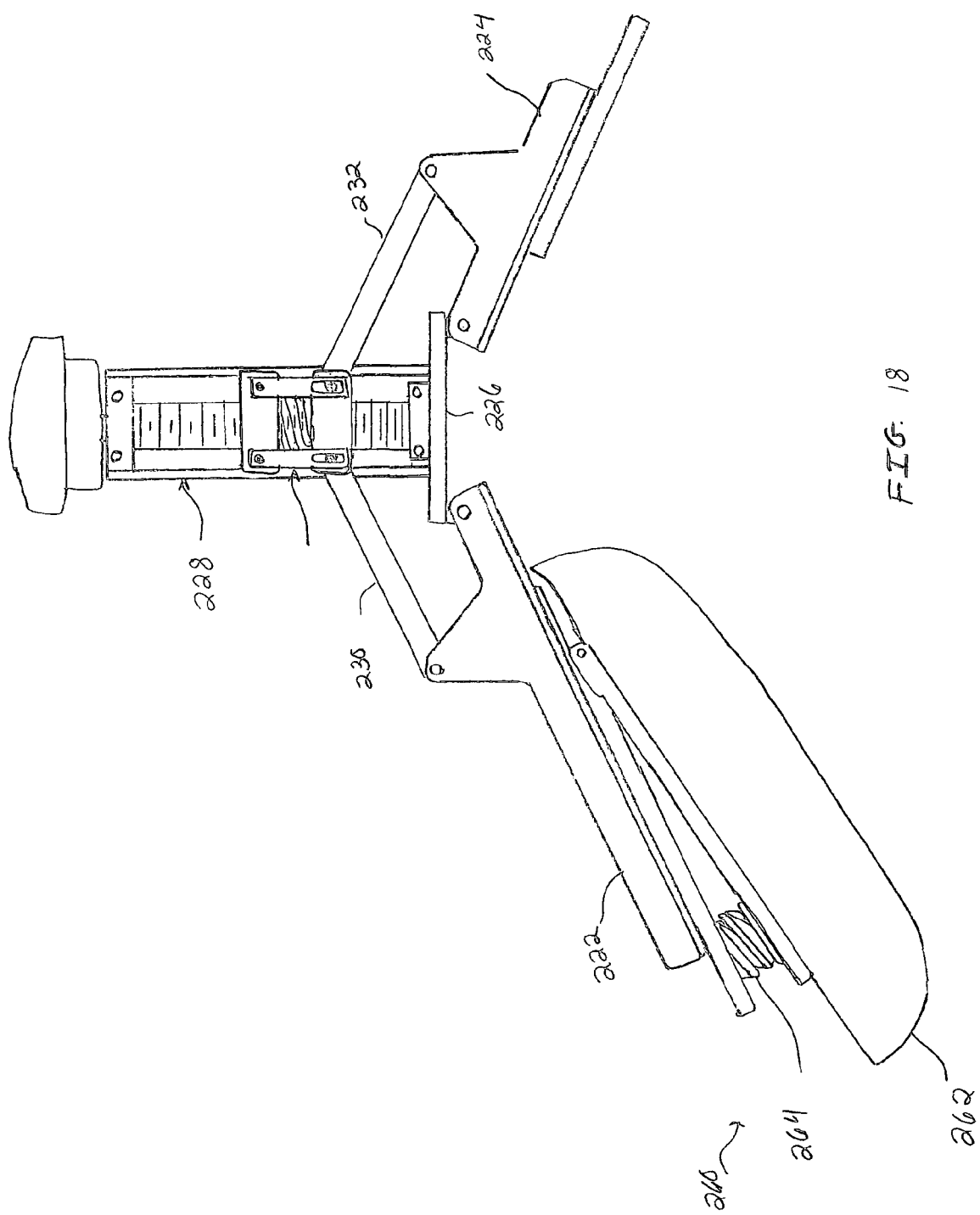
FIG. 18 depicts an orthosis of the present invention including a first and second force application assembly.

Referring to FIG. 18, the orthosis 220 can further include a second force application assembly 260. The force application assembly 260 can take the form as those previously described herein. For example, the force application assembly 260 includes an assembly member 262 pivotally connected to the first arm member 222, such that the assembly member 262 is interposed between the first arm member 222 and the first body portion. One or more force elements 264, such as a spring, is interposed between the first arm member 222 and the assembly member 262, where the force element 264 provides a force urging the assembly member 262 away from the first arm member 222.

Initially, the force applied by the force application assemblies 236 and 260 may be less than a force applied by the drive assembly 234. As the tissue is stretched, the tissue relaxes lowering the force in the tissue imparted by the drive assembly 234. The drive assembly force may decrease to a point where the force application assembly force exceeds the drive assembly force, such that the force application assemblies 236 and 260 can provide a force to the tissue. In one embodiment, the force application assemblies 236 and 260 can impart a substantially constant force onto the second body portion. The application of the force application assembly forces utilizes the principals of creep to continuous stretch the joint tissue during the set time period, maintiain, decreasing, or preventing a relaxation of the tissue.

After a set time period, the drive assembly 16 may be used to move the second arm member 14 with respect to the first arm member 12 from the second position to a third position, incrementally stretching the tissue surrounding the joint. It is contemplated that the drive assembly 12 may be used to incrementally move the second body portion after the expiration of a predetermined time or until completion of the protocol.

As previously discussed, when a joint is flexed or extended a compressive or distractive force may be applied to the connective tissue surrounding the joint. The compressive or distractive force may be controlled by slidably mounting the cuffs to the arm members. Alternatively, the arm members can be expandable to adsorb the compressive and distractive forces imparted in the joint.

Figure 19:
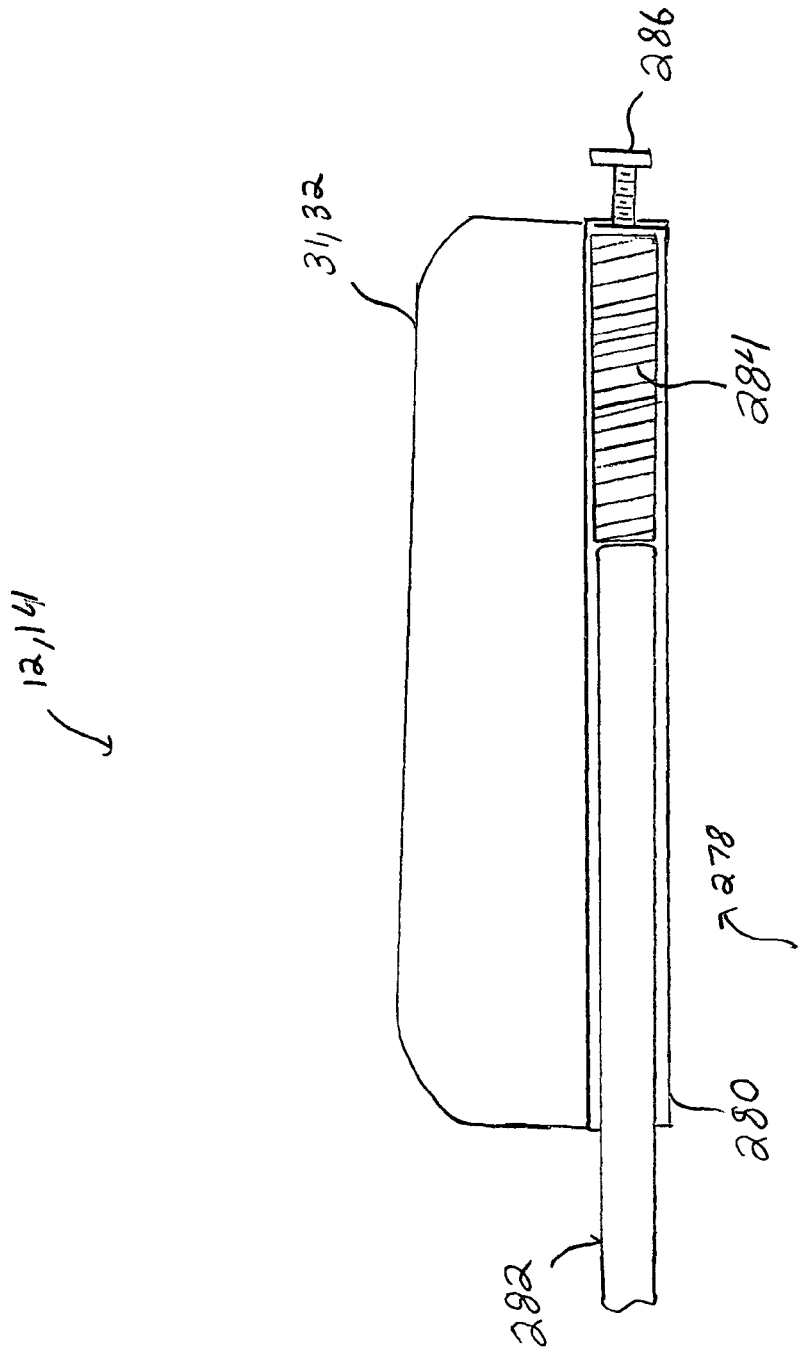
FIG. 19 depicts a telescoping arm member for the orthosis of the present invention.

Referring to FIG. 19, arm member 12 or 14 may include a telescoping rod 278 having a first portion 280 slidably mounted onto a second portion 282. Each arm member 12 or 14 can include a cuff 31 or 32 mounted to the first portion 280, where the cuff 31 or 32 clamps onto a body portion on either side of the joint. Movement of the arm member 12 or 14 to extend the joint may result in distractive forces being applied to the joint. These distractive forces are limited and controlled by the first member 280 sliding on the second member 282. The first member 280 is selectively moved along the second member 282, during relative movement of the arm member 12 or 14, to provide the proper amount of distractive forces to the joint and to limit compressive forces on the joint.

In addition to controlling the compressive and distractive forces, the telescoping rod 278 can be used to adjust the length of the arm member 12 or 14. Adjustment of the arm member 12 or 14 enables the orthosis to be better tailored to a user's anatomy.

Additionally, a spring 284 can be interposed between the first and second portions 280 and 282. The spring 284 can provide a distractive force to the joint. The amount of force applied by the spring can be controlled using a control mechanism. The control mechanism can include a threaded member 286 which can be used to increase or decrease the applied force.

Furthermore, as the spring 284 provides a distractive force, expanding the telescoping rod 278 imparts a moment force about the joint axis. The moment imparts a substantially constant force to the first and second arm members 12 and 14 and the second body portion, utilizing the principles of creep to further stretch the joint tissue.

It should be understood that the orthosis of the present invention can be used to extend, flex, or rotate other joints in the body, such as an ankle, knee, finger, wrist, or elbow joint, with the construction of the orthosis in such case being varied to fit the particular application. The orthosis can be used, for example, to flex the ankle joint to stretch a tight achilles tendon in cerebral palsy or post traumatic contractures. It may also be especially useful in obtaining the last degrees of joint extension. The orthosis can be custom made to fit a particular individual, or can be an off the shelf item. The orthosis can also be used, for example, to eliminate contractures or stress soft tissue. It can be used for patients with cerebral palsy, stroke, spastic paralysis, burns, as well as in post-traumatic or post-surgical cases. It can also be used, for example, in therapy after a knee replacement, in which the extremes of motion in extension or flexion are difficult to obtain without extensive intervention of a therapist. As previously discussed, the invention also may be used to extend the rotational capability of a joint.

Additionally, as noted above, the device can be used for tissue transport, bone lengthening, stretching skin or tissue fascia, etc. For example, device of the present invention can be incorporated in an external bone fixation device, such as a llizarov device, where the device is affixed to the bones on the body portions using pins. The drive assembly and force application assembly can be used for bone lengthening and stretch the surround soft tissue.

Furthermore, the present invention is disclosed as utilizing the principles of stress relaxation and creep. However, it is contemplated that the present invention can include additional treatment protocols. For example, in continuous passive motion ("CPM"), the device continually moves the joint through a range of motion. The motion may be provided by an electric or hydraulic motor or a pneumatic system attached to the device. As the CPM moves the joint through its range of motion, however, it does not increase the range of motion.

The present invention can be incorporated into a CPM device, where the CPM device would stop at an end range position. As previously discussed, a drive assembly may be provided to move the joint from its normal position at the end range position of the CPM to a second position, thereby stretching the tissue using the principles of stress relaxation. As the tissue relaxes, a force application assembly may be utilized to provide an additional force, utilizing the principles of creep to stretch the tissue. After a set time period, the drive assembly may be moved to a third position to further stretch the tissue or the CPM device may resume movement of the joint throughout the range of motion. Before CPM movement resumes, the drive assembly may be returned to an original position so that the range of motion of the CPM is returned to its original state, or the drive assembly may be used to alter the range of motion that the CPM follows. In this manner CPM device can be utilized to increase the range of motion of the joint.

Figure 20:
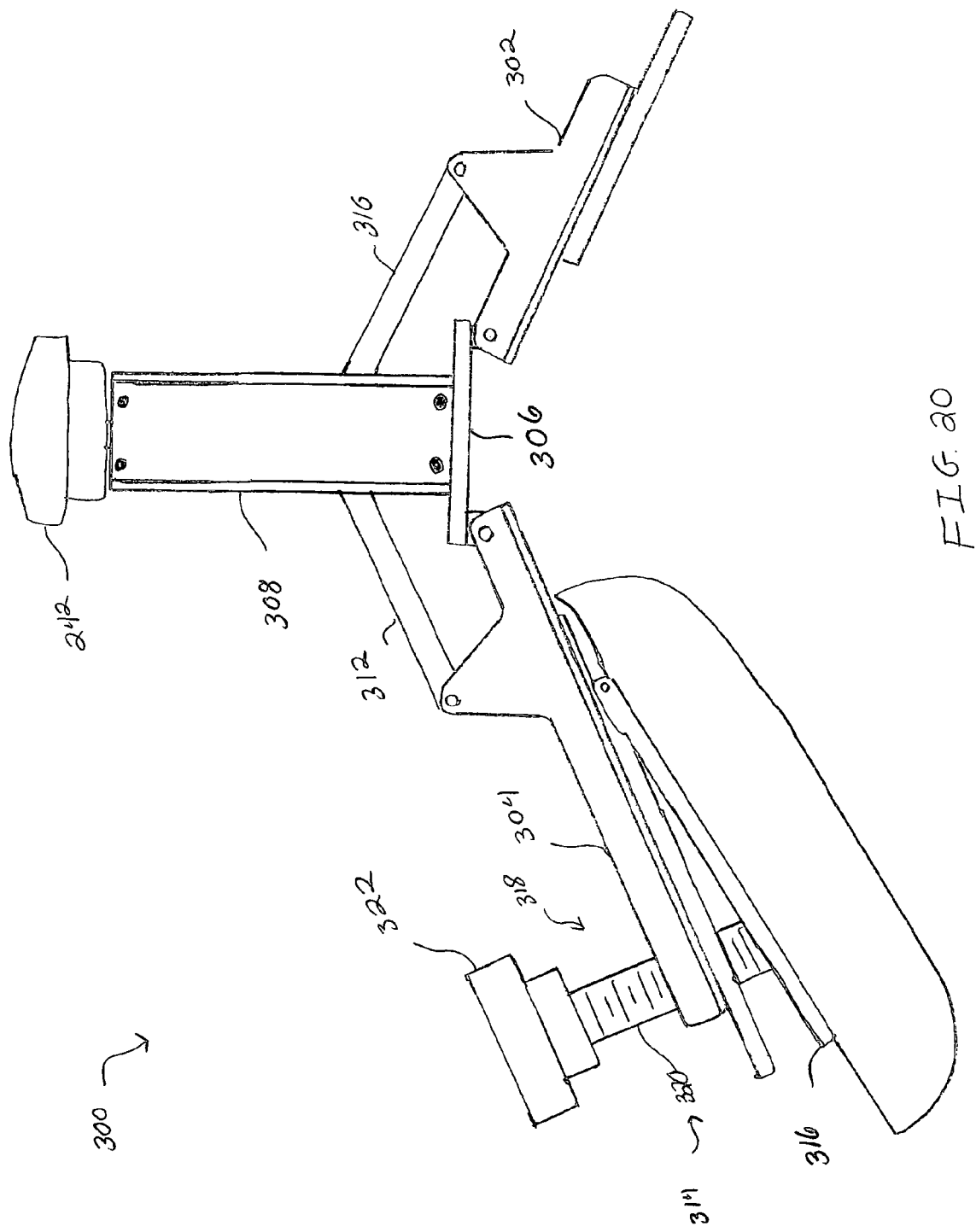
FIG. 20 depicts an orthosis of the present invention including multiple drive assemblies.

In a further embodiment, the device of the present invention can include multiple drive assemblies for providing a macro and micro adjustment of the device. Referring to FIG. 20 another orthosis 300 of the present invention is provided. The orthosis 300 includes first and second arm members 302 and 304 pivotally connected to a base member 306. A first drive assembly 308 is mounted to the base member 306 proximal to the first and second arm members 302 and 304. The first arm member 302 is operably connected to the first drive assembly 308 with a first lever arm 310 and the second arm member 304 is operably connected to the first drive assembly 308 with a second lever arm 312, such that an operation of the first drive assembly 308 pivots the first and second lever arms 302 and 304 about the base member 306.

As describe above in FIG. 16, The first drive assembly 308 can include a thread member 238 rotatably mounted in a control frame 240, where a first end of the threaded member 238 in rotatable connected to the base member 306 and a second end of the threaded member 238 is connect to a knob 242, such that a rotation of the knob 242 rotates the threaded member 238. A threaded bushing 244 is slidably mounted in the control frame 240 about the threaded member 238, such that rotation of the threaded member 238 caused the threaded bushing 244 to traverse the threaded member 238. The first drive assembly 308 provides a macro or gross adjustment of the first and second arm members 302 and 304. In use, this drive member may implement principles of stress relaxation by moving the joint or tissue from a first position to a second position that is maintained while the tissue stretches.

A second drive assembly 314 is mounted to the second arm member 304. The second drive assembly 314 includes an assembly member 316 pivotally connected to the second arm member 304. A drive element 318 in interposed between the assembly member 316 and the second arm member 304. The drive element 318 provides a force to the assembly member 316 and the second arm member 304, such that the position of the assembly member 316 can be moved and selectively positioned with respect to the second arm member 304. The drive element 318 provides a micro or fine adjust to the device and may be used to utilize the principles of creep by imparting forces to the joint while the first drive assembly 308 is held in a fixed position.

Thus, once the first drive assembly moves the joint or tissue to a second position, the second drive assembly may impart loading on the tissue or joint. This loading can be provided by monitoring resistive forces of the tissue and adjusting the device to maintain a desired loading condition. Thus, over time the position of the second drive assembly may change while the position of the first drive assembly remains fixed. If the first drive assembly is subsequently moved to a third position, the second drive assembly may also be repositioned to an original or starting position with respect to the second arm member 304.

The drive element 318 can include a threaded member 320 threaded through the second arm member 304. A first end of the threaded member 320 contact a bottom surface of the assembly member 316. A second end of the threaded member 320 includes a knob 322, a rotation of which threaded the threaded member 320 through the second arm member 304 changes the position of the assembly member 316 with respect to the second arm member 304.

Alternatively, the drive element 318 can be a gear system or pneumatic device positioned between the assembly member 316 and the second arm member 304. The gear system or pneumatic device can provide a force to change the position of the assembly member 316 with respect to the second arm member 304.

In the previous embodiment the first and second arm members are shown being connected by a simple connector, pivoting about a singly axis. However, it is contemplated the s first and second arm member can be connect by a complex connector, allowing rotation about multiple axis. For example, the complex connect can be a ball and socket type joint, a universal joint, or other similar type joints.

Figure 21:
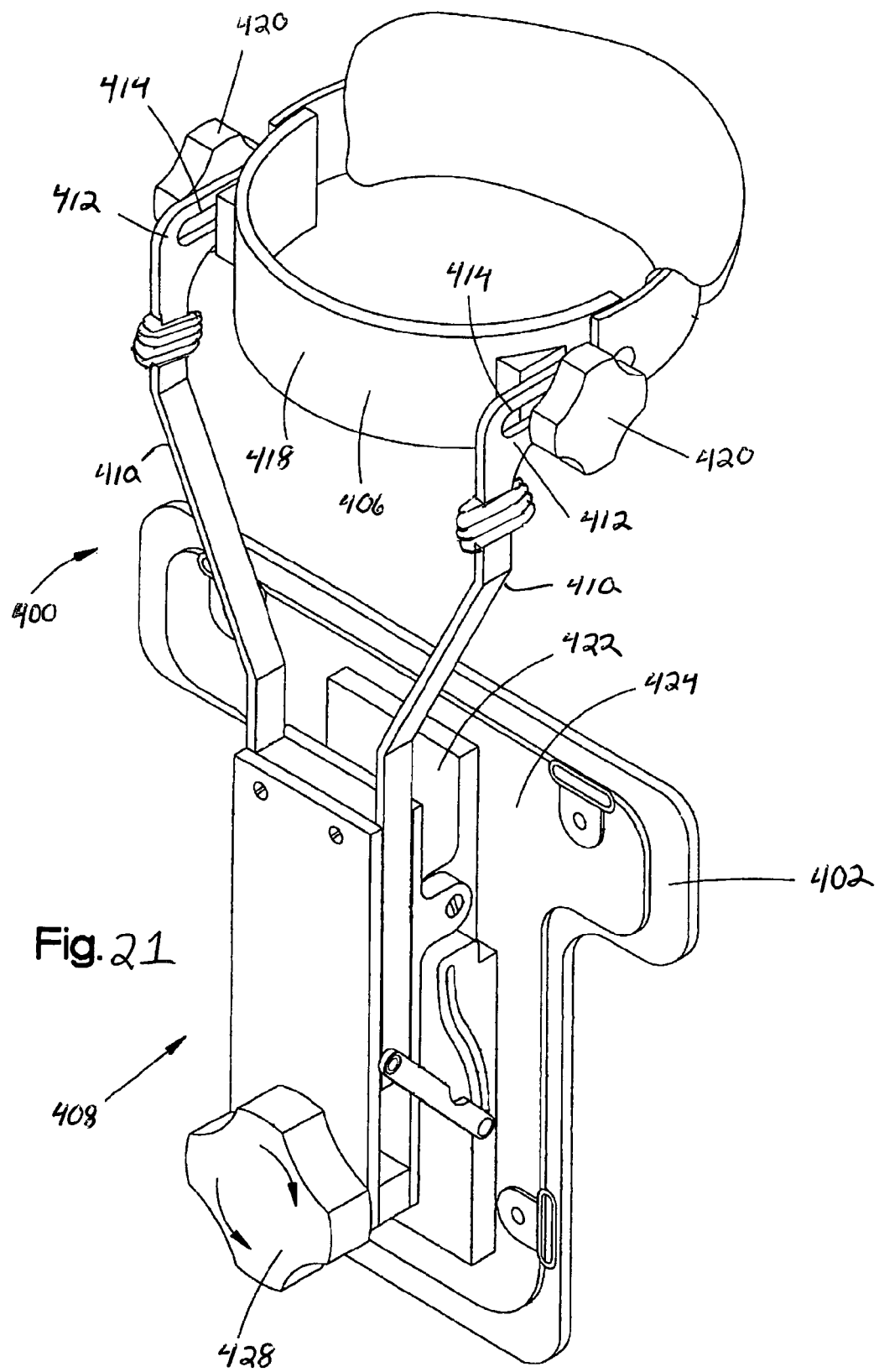
FIG. 21 depicts a neck orthosis in accordance with the present invention.

Referring to FIG. 21, neck brace 400 can be used to move or stabilize a neck of a patient. The neck brace 400 includes a T-shaped support member 402 which is connected with a torso 404 of a person. A chin support 406 is connected with a chin of the person. An actuator mechanism 408 moves the chin support 406 relative to the support member 402. The chin support 406 is moved relative to the support member 402 after the chin support is connected to the chin and the support member is connected to the torso 404 to move the neck of the person. The support member 402 and the chin support 406 may have any desired construction as long as they are effective to engage the torso 404 and the chin.

A pair of interconnecting members or arms 410 connects the chin support 406 with the support member 402. The arms 410 extend from the chin support 406 to the actuator mechanism 408. Each of the arms 410 has an upper end 412 with a slot 414. Threaded members 416 extend from the portion 418 of the chin support 406 through the slots 414. Clamping members 420 threadably engage the threaded members 416 to clamp the ends 412 of the arms 410 to the portion 418. The portion 418 can be positioned relative to the arms 410 when the clamping members 420 are loosened from the threaded members 416. The portion 418 can be pivoted about the threaded members 416 and the threaded members can be moved between the ends of the slots 414 to position the chin support 406 relative to the arms 410.

The actuator mechanism 408 is connected to a pivot support 422 connected to a support plate 424 of the support member 402. The actuator mechanism 408 is connected to the pivot support by a pivot connection 426. The actuator mechanism 408 transmits force between the support member 402 and the chin support 406 to simultaneously pivot the actuator mechanism about a pivot axis of the pivot connection 426 and move the interconnecting members 410 relative to the actuator mechanism.

The actuator mechanism 408 transmits force from an input member which, in the illustrated embodiment of the neck brace 400, is a manually rotatable knob 428. Force is transmitted from the knob 428 through the actuator mechanism 408 to the chin support 406. Force is transmitted from the actuator mechanism 408 to pivot the actuator mechanism about the pivot connection 426. In addition, force is transmitted from the knob 428 to move the interconnecting members 410 and the chin support 406 relative to the actuator mechanism 408 as the actuator mechanism pivots about the pivot connection 426. The neck brace 400 is more fully described in U.S. Pat. No. 6,503,213, entitled Method of Using a Neck Brace, to Bonutti, the entire contents of which are herein incorporated by reference in its entirety.

The interconnecting arms 410 further include a force application assembly 430. The arms 410 are bisected into first and second portions 432 and 434, where the force application assembly 430 is interposed between the first and second portions 432 and 434. The force application assembly 430 can provided a force to the second portion 434 with respect to the first portion 432, such that a distractive force can be applied to the neck of the patient. For example, the distractive force provides a cervical traction to the neck of the patient, separating the vertebrae.

As previously discussed, the force application assembly can include a spring portion, bladder or other such mechanism. Additionally, the applied force can be selectively controlled, where the magnitude of the applied force can be increased or decreased by the patient, medical practitioner, or others.

The components of the present invention are rigid members made of, for example, aluminum, stainless steel, polymeric, or composite materials. The member and extensions are rigid so as to be able to transmit the necessary forces. It should be understood that any material of sufficient rigidity can be used.

For example, the components can be made by injection molding. Generally for injection molding, tool and die metal molds of the components are prepared. Hot, melted plastic material is injected into the molds. The plastic is allowed to cool, forming components. The components are removed from the molds and assembled.

Furthermore, it is contemplated that the components can be made of polymeric or composite materials such that the device can be disposable. For example, at least some or all of the components can be made of a biodegradable material such as a biodegradable polymer. Among the important properties of these polymers are their tendency to depolymerize relatively easily and their ability to form environmentally benign byproducts when degraded or depolymerized. One such biodegradable material is poly (hydroxyacids) ("PHA's") such as polyactic acid ("PLA") and polyglycolic acid ("PGA").

Additionally, the device can be made of a nonmagnetic material. In such instance, the device can be used as a positioning device for use in imaging devices, such as a MRI device. It is also contemplated that the device can be used as a positioning device for use during surgical procedures, where it may be necessary to adjust and hold the position of the joint.

All references cited herein are expressly incorporated by reference in their entirety.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method for incrementally increasing the range of motion of first and second body portions of a joint, the method comprising:

connecting a first arm member with the first body portion;

connecting a second arm member with the second body portion, wherein the first and second arm members are movably connected relative to each other to be able to form a range of angles therebetween, and wherein a force imparting member interposes the second arm member and the second body portion;

rotating the first arm member to move from a first position to a second position, to change an angle formed between the first and second arm members;

restricting, at least partially, movement of the first and second arm members from the second position towards the first position; and moving the second body portion away from the second arm member by applying a first force to the second body portion, using the force imparting member, the first force operative to urge the second body portion away from the second arm member.

2. A method as set forth in claim 1 wherein the joint and the first and second body portions define on one side of the joint an inner sector which decreases in angle as the second arm member is moved from the first position to the second position.

3. A method as set forth in claim 2 wherein applying the first force to the second body portion includes decreasing the angle of the inner sector after the second arm member is moved into the second arm position.

4. A method as set forth in claim 1 wherein the joint and the first and second body portions define on one side of the joint an outer sector which decreases in angle as the second arm member is moved from the first position to the second position.

5. A method as set forth in claim 4 wherein applying the first force to the second body portion includes increasing the angle of the outer sector after the second arm member is moved into the second arm position.

6. A method as set forth in claim 1, further comprising:
moving the second arm member from the second position to a third position with respect to the first arm member, using a drive mechanism, the third position being farther from the first position than the second position;
restricting, at least partially, movement of the second arm member from the third position towards the second position; and
applying a second force to the second body portion, using the force imparting member, the second force being operative to further urge the second body portion away from the second arm member.

7. The method of claim 1, wherein said steps of moving, restricting, and applying, are repeated.

8. The method of claim 1, wherein the force imparting member includes at least one of a motor, a pressurized bladder, a piston, a hydraulic system, and a pneumatic system.

9. The method of claim 1, wherein the force imparting member includes at least one of a spring, a fluid bladder, an elastic material, and a resilient material.

10. The method of claim 1, wherein the force imparting member includes at least one of a pneumatic system, a hydraulic system, an open cell foam, a closed cell foam, a rubber, a urethane, and a plastic.

11. The method of claim 1, wherein the joint includes at least one of an ankle, a knee, a finger, a wrist, and an elbow.

12. The method of claim 1, wherein rotating the first and second arm members from a first position to a second position comprises simultaneously rotating the first and second arm members from a first position to a second position.

13. A method for increasing the range of motion of a joint by incrementally stretching connective tissue between first and second body portions of said joint, the method comprising:
connecting a first arm member with the first body portion;
connecting the second body portion to a force imparting member, the force imparting member movably coupled to a second arm member, wherein the first and second arm members are pivotally connected;
rotating the first arm member with respect to the joint to move from a first position to a second position, wherein rotating the first arm member induces rotation in the second arm member to move from the first position to the second position;
rotating the second arm member with respect to the joint to move from a first position to a second position;

restricting, at least partially, movement of the second arm member with respect to the first arm member from the second position towards the first position; and
stretching the connective tissue using a first creep force exerted between the second body portion and the second arm member by the force imparting member, the first creep force being operative to urge the second body portion away from the first position while leaving the second arm member substantially in the second position.

14. A method as set forth in claim 13, further comprising:
moving the second arm member from the second position to a third position with respect to the first arm member, wherein the second body portion is rotated further with respect to the first body portion;
restricting, at least partially, movement of the second arm member with respect to the first arm member from the third position towards the second position; and
applying a second creep force to the second body portion using the force imparting member after the second body portion is rotated further with respect to the first arm member, the second creep force being operative to urge the second body portion farther away from the first position.

15. A method as set forth in claim 13, wherein said moving is carried out using a gear system and said creep force is applied by at least one spring.

16. The method of claim 13, wherein the first creep force remains substantially constant, decreases, or increases over time.

17. The method of claim 13, wherein the force imparting member includes at least one of a motor, a pressurized bladder, a piston, a hydraulic system, and a pneumatic system.

18. The method of claim 13, wherein the force imparting member includes at least one of a spring, a fluid bladder, an elastic material, and a resilient material.

19. The method of claim 13, wherein the force imparting member includes at least one of a pneumatic system, a hydraulic system, an open cell foam, a closed cell foam, a rubber, a urethane, and a plastic.

20. The method of claim 13, wherein the joint includes at least one of an ankle, a knee, a finger, a wrist, and an elbow.

21. The method of claim 13, wherein rotating the first and second arm members with respect to the joint from a first position to a second position comprises simultaneously rotating the first and second arm members with respect to the joint from a first position to a second position.

22. A method for increasing the range of motion of a joint stretching connective tissue between first and second body portions of said joint, the method comprising:
operating a drive mechanism of an orthosis comprising a first arm member coupled to the first body portion and a second arm member coupled to the second body portion to rotate the first arm member and the second arm member relative to the joint to cause relative movement between the first and second body portions from a first position to a second position wherein, in the second position, a force application member is elastically deformable by an initial force imposed by the orthosis on the first body portion and the second body portion;
reducing operation of the drive mechanism; and
moving the first and second body portions relative to joint from the second position to a third position, the third position being farther from the first position than the second position, wherein the first and second body portions are moved by applying a creep force to the first body portion and the second body portion using the elastically deformable force application member while operation of the drive mechanism is reduced.

23. A method as set forth in claim 22, wherein said drive mechanism includes a gear system and said force application member includes at least one spring.

24. The method of claim 22, wherein the creep force remains substantially constant, decreases, or increases over time.

25. The method of claim 22, wherein the force application member includes at least one of a motor, a pressurized bladder, a piston, a hydraulic system, and a pneumatic system.

26. The method of claim 22, wherein the force application member includes at least one of a spring, a fluid bladder, an elastic material, and a resilient material.

27. The method of claim 22, wherein the force application member includes at least one of a pneumatic system, a hydraulic system, an open cell foam, a closed cell foam, a rubber, a urethane, and a plastic.

28. The method of claim 22, wherein the joint includes at least one of an ankle, a knee, a finger, a wrist, and an elbow.

29. The method of claim 22, wherein operating a drive mechanism of an orthosis comprising a first arm member coupled to the first body portion and a second arm member coupled to the second body portion to rotate the first arm member and the second arm member relative to the joint comprises operating a drive mechanism of an orthosis comprising a first arm member coupled to the first body portion and a second arm member coupled to the second body portion to simultaneously rotate the first arm member and the second arm member relative to the joint.

30. A method for incrementally increasing the range of motion of first and second body portions of a joint, the method comprising:

connecting a first arm member with the first body portion;
connecting a second arm member with the second body portion, wherein the first and second arm members are movably connectable relative to each other to form a range of angles therebetween;
rotating the first arm member to move from a first position to a second position with respect to the joint, using a drive mechanism associated with the first arm member, to change an angle formed between the first and second arm members, wherein rotating the first arm member induces rotation in the second arm member to move from the first position to the second position, using a drive mechanism associated with the second arm member, to change an angle formed between the first and second arm members;
restricting, at least partially, movement of the second arm member with respect to the first arm member only in a direction from the second position towards the first position; and
applying a force to the second body portion, using a force imparting member associated with the first and second arms, operative to urge the second body portion away from the second arm member.

31. The method of claim 30, wherein said steps of moving, restricting, and applying, are repeated.

32. The method of claim 30, wherein the force imparting member includes at least one of a motor, a pressurized bladder, a piston, a hydraulic system, and a pneumatic system.

33. The method of claim 30, wherein the force imparting member includes at least one of a spring, a fluid bladder, a elastic material, and a resilient material.

34. The method of claim 30, wherein the force imparting member includes at least one of a pneumatic system, a hydraulic system, an open cell foam, a closed cell foam, a rubber, a urethane, and a plastic.

35. The method of claim 30, wherein the joint includes at least one of an ankle, a knee, a finger, a wrist, and an elbow.

* * * * *